(12) United States Patent
Tournier-Lasserve et al.

(10) Patent No.: US 7,138,234 B2
(45) Date of Patent: Nov. 21, 2006

(54) GENE INVOLVED IN CADASIL, METHOD OF DIAGNOSIS AND THERAPEUTIC APPLICATION

(75) Inventors: Elisabeth Tournier-Lasserve, Paris (FR); Anne Joutel, Paris (FR); Marie-Germaine Bousser, Paris (FR); Jean-François Bach, Paris (FR)

(73) Assignees: Institut National de la Sante et de la Recherche Medicale (INSERM), Paris (FR); Assistance Publique-Hopitaux de Paris, Paris (FR)

( * ) Notice: Subject to any disclaimer, the term of this patent is extended or adjusted under 35 U.S.C. 154(b) by 258 days.

(21) Appl. No.: 10/356,625

(22) Filed: Feb. 3, 2003

(65) Prior Publication Data

US 2003/0186290 A1    Oct. 2, 2003

Related U.S. Application Data

(62) Division of application No. 09/230,652, filed as application No. PCT/FR97/01433 on Jan. 29, 1999.

(30) Foreign Application Priority Data

Aug. 1, 1996   (FR) .................................. 96 09733
Apr. 16, 1997  (FR) .................................. 97 04680

(51) Int. Cl.
    *C12Q 1/68*    (2006.01)
    *C12P 21/06*   (2006.01)
    *C12P 19/34*   (2006.01)

(52) U.S. Cl. ...................... 435/6; 435/69.1; 435/91.1; 435/91.2

(58) Field of Classification Search .............. None
See application file for complete search history.

(56) References Cited

FOREIGN PATENT DOCUMENTS

CA          2116628      2/1994

OTHER PUBLICATIONS

Munoz et al., Can. Med. Assoc. Journal 162: 65-72, 2000.*
Burgess et al., *The Journal of Cell Biology*, 111:2129-2138 (1990).
Ducros et al., "Cerebral Autosomal Dominant Arteriopathy With Subcortical Infarcts and Leukoencephalopathy, Genetic Homogeneity, and Mapping of the Locus Within a 2-cM Interval", *Am. J. Hum. Genet.* 58:171-181 (1996).
Joutel et al., "Notch3 Mutations in CADASIL, a Hereditary Adult-Onset Condition Causing Stroke and Dementia", *Nature* 383:707-710.
Joutel et al., "Identification of the CADASIL Gene", *Stroke* 28(1):246, Abstract 65 (1997).
Joutel et al., "Identification of Expressed Sequences From the CADASIL Region on 19p", *Amer. J. of Human Genet.* 57(3):A342, Abstract 1985 (1995).
Lardelli et al., "Expression of the Notch 3 Intracellular Domain in Mouse Central Nervous System Progenitor Cells is Lethal and Leads to Disturbed Neural Tube Development", *Mech. of Develop.* 59:177-190 (1996).
Lardelli et al., "The Novel Notch Homologue Mouse Notch 3 Lacks Specific Epidermal Growth Factor-Repeats and is Expressed in Proliferating Neuroepithelium", *Mech. of Develop.* 46:123-136 (1994).
Larsson, C., et al., "The Human NOTCH1, 2, and 3 Genes Are Located at Chromosome Positions 9q34, 1p13-p11, and 19p.13.2-p13.1 in Regions of Neoplasia-Associated Translocation," *Genomics* 24(2):253-258 (1994).
Lindsell et al., "Expression Patterns of Jagged, Delta1, Notch1, Notch2, and Notch3 Genes Identify Ligand-Receptor Pairs That May Function in Neural Development", *Mol. and Cell. Neuroscience* 8:14-27 (1996).
Ophoff et al., "Gene for Familial Hemiplegic Migraine on Chromosome 19p13", *Posters: Molecular Etiology of Disease*, vol. 57, No. 4, pp. A222, Abstract 1284 (1995).
Rudinger et al., in "Peptide Hormones", edited by Parsons, J.A., University Park Press, Jun. 1976, p. 6.
Sambrook, J., et al., "Molecular Cloning, A Laboratory Manual," $2^{nd}$, 16.1-16.81 (1989).
Bork, Peer et al., "Sequences and Topology Deriving Biological Knowledge from Genomic Sequences," *Current Opinion in Structural Biology*, vol. 8, pp. 331-322 (1998).
Del Amo, Francisco Franco et al., "Expression Pattern of Motch, a Mouse Homolog of Drosophila Notch, Suggest and Important Role in Early Postimplantation Mouse Development," vol. 115, pp. 737-744 (1992).
Skolnick, Jeffrey et al., "From Genes to Protein Structure and Function: Novel Applications of Computational Approaches in the Genomic Era," *Trends in Biotech.*, vol. 18(1), pp. 34-39 (2000).

* cited by examiner

*Primary Examiner*—Eileen O'Hara
*Assistant Examiner*—Gyan Chandra
(74) *Attorney, Agent, or Firm*—Finnegan, Henderson, Farabow, Garrett and Dunner, L.L.P.

(57) ABSTRACT

The invention concerns the Notch3 gene and the corresponding protein, which are involved in CADASIL. The invention concerns, in particular, methods for demonstrating mutations in this gene, which are linked to the risk of developing CADASIL and related diseases.

22 Claims, 11 Drawing Sheets

Figure 3:
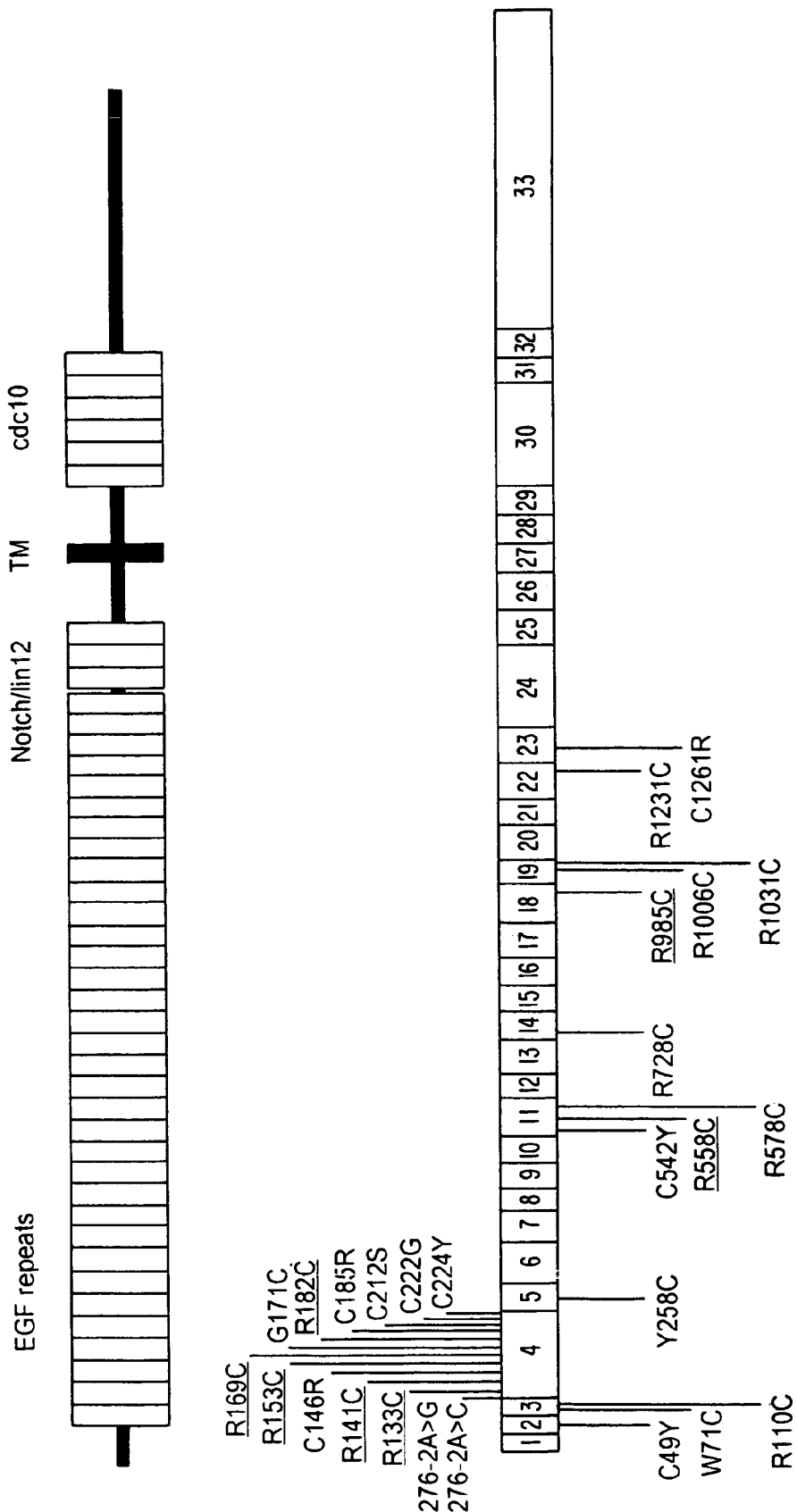

```
  2                      17                     32
ACG CGG CGC GGA GGC TGG CCC GGG ACG CGC CCG GAG CCC AGG GAA
 47                      62                     77
GGA GGG AGG AGG GGA GGG TCG CGG CCG GCC GCC ATG GGG CCG GGG
                                             M   G   P   G
 92                     107                    122
GCC CGT GGC CGC CGC CGC CGC CGT CGC CCG ATG TCG CCG CCA CCG
 A   R   G   R   R   R   R   R   R   P   M   S   P   P   P
137                     152                    167
CCA CCG CCA CCC GTG CGG GCG CTG CCC CTG CTG CTG CTG CTA GCG
 P   P   P   P   V   R   A   L   P   L   L   L   L   L   A
182                     197                    212
GGG CCG GGG GCT GCA GCC CCC CCT TGC CTG GAC GGA AGC CCG TGT
 G   P   G   A   A   A   P   P   C   L   D   G   S   P   C
227                     242                    257
GCA AAT GGA GGT CGT TGC ACC CAG CTG CCC TCC CGG GAG GCT GCC
 A   N   G   G   R   C   T   Q   L   P   S   R   E   A   A
272                     287                    302
TGC CTG TGC CCG CCT GGC TGG GTG GGT GAG CGG TGT CAG CTG GAG
 C   L   C   P   P   G   W   V   G   E   R   C   Q   L   E
317                     332                    347
GAC CCC TGT CAC TCA GGC CCC TGT GCT GGC CGT GGT GTC TGC CAG
 D   P   C   H   S   G   P   C   A   G   R   G   V   C   Q
362                     377                    392
AGT TCA GTG GTG GCT GGC ACC GCC CGA TTC TCA TGC CGG TGC CCC
 S   S   V   V   A   G   T   A   R   F   S   C   R   C   P
407                     422                    437
CGT GGC TTC CGA GGC CCT GAC TGC TCC CTG CCA GAT CCC TGC CTC
 R   G   F   R   G   P   D   C   S   L   P   D   P   C   L
452                     467                    482
AGC AGC CCT TGT GCC CAC GGT GCC CGC TGC TCA GTG GGG CCC GAT
 S   S   P   C   A   H   G   A   R   C   S   V   G   P   D
497                     512                    527
GGA CGC TTC CTC TGC TCC TGC CCA CCT GGC TAC CAG GGC CGC AGC
 G   R   F   L   C   S   C   P   P   G   Y   Q   G   R   S
542                     557                    572
TGC CGA AGC GAC GTG GAT GAG TGC CGG GTG GGT GAG CCC TGC CGC
 C   R   S   D   V   D   E   C   R   V   G   E   P   C   R
587                     602                    617
CAT GGT GGC ACC TGC CTC AAC ACA CCT GGC TCC TTC CGC TGC CAG
 H   G   G   T   C   L   N   T   P   G   S   F   R   C   Q
632                     647                    662
TGT CCA GCT GGC TAC ACA GGG CCA CTA TGT GAG AAC CCC GCG GTG
 C   P   A   G   Y   T   G   P   L   C   E   N   P   A   V
677                     692                    707
CCC TGT GCG CCC TCA CCA TGC CGT AAC GGG GGC ACC TGC AGG CAG
 P   C   A   P   S   P   C   R   N   G   G   T   C   R   Q
722                     737                    752
AGT GGC GAC CTC ACT TAC GAC TGT GCC TGT CTT CCT GGG TTT GAG
 S   G   D   L   T   Y   D   C   A   C   L   P   G   F   E
767                     782                    797
GGT CAG AAT TGT GAA GTG AAC GTG GAC GAC TGT CCA GGA CAC CGA
 G   Q   N   C   E   V   N   V   D   D   C   P   G   H   R
812                     827                    842
TGT CTC AAT GGG GGA ACA TGC GTG GAT GGC GTC AAC ACC TAT AAC
 C   L   N   G   G   T   C   V   D   G   V   N   T   Y   N
857                     872                    887
TGC CAG TGC CCT CCT GAG TGG ACA GGC CAG TTC TGC ACG GAG GAC
 C   Q   C   P   P   E   W   T   G   Q   F   C   T   E   D
902                     917                    932
GTG GAT GAG TGT CAG CTG CAG CCC AAC GCC TGC CAC AAT GGG GGT
 V   D   E   C   Q   L   Q   P   N   A   C   H   N   G   G
947                     962                    977
ACC TGC TTC AAC ACG CTG GGT GGC CAC AGC TGC GTG TGT GTC AAT
 T   C   F   N   T   L   G   G   H   S   C   V   C   V   N
992                    1007                   1022
GGC TGG ACA GGT GAG AGC TGC AGT CAG AAT ATC GAT GAC TGT GCC
 G   W   T   G   E   S   C   S   Q   N   I   D   D   C   A
```

FIG. 1A

```
1037                1052                1067
ACA GCC GTG TGC TTC CAT GGG GCC ACC TGC CAT GAC CGC GTG GCT
 T   A   V   C   F   H   G   A   T   C   H   D   R   V   A
1082                1097                1112
TCT TTC TAC TGT GCC TGC CCC ATG GGC AAG ACT GGC CTC CTG TGT
 S   F   Y   C   A   C   P   M   G   K   T   G   L   L   C
1127                1142                1157
CAC CTG GAT GAC GCC TGT GTC AGC AAC CCC TGC CAC GAG GAT GCT
 H   L   D   D   A   C   V   S   N   P   C   H   E   D   A
1172                1187                1202
ATC TGT GAC ACA AAT CCG GTG AAC GGC CGG GCC ATT TGC ACC TGT
 I   C   D   T   N   P   V   N   G   R   A   I   C   T   C
1217                1232                1247
CCT CCC GGC TTC ACG GGT GGG GCA TGT GAC CAG GAT GTG GAC GAG
 P   P   G   F   T   G   G   A   C   D   Q   D   V   D   E
1262                1277                1292
TGC TCT ATC GGC GCC AAC CCC TGC GAG CAC TTG GGC AGG TGC GTG
 C   S   I   G   A   N   P   C   E   H   L   G   R   C   V
1307                1322                1337
AAC ACG CAG GGC TCC TTC CTG TGC AGG TGC GGT CGT GGC TAC ACT
 N   T   Q   G   S   F   L   C   Q   C   G   R   G   Y   T
1352                1367                1382
GGA CCT CGC TGT GAG ACC GAT GTC AAC GAG TGT CTG TCG GGG CCC
 G   P   R   C   E   T   D   V   N   E   C   L   S   G   P
1397                1412                1427
TGC CGA AAC CAG GCC ACG TGC CTC GAC CGC ATA GGC CAG TTC ACC
 C   R   N   Q   A   T   C   L   D   R   I   G   Q   F   T
1442                1457                1472
TGT ATC TGT ATG GCA GGC TTC ACA GGA ACC TAT TGC GAG GTG GAC
 C   I   C   M   A   G   F   T   G   T   Y   C   E   V   D
1487                1502                1517
ATT GAC GAG TGT CAG AGT AGC CCC TGT GTC AAC GGT GGG GTC TGC
 I   D   E   C   Q   S   S   P   C   V   N   G   G   V   C
1532                1547                1562
AAG GAC CGA GTC AAT GGC TTC AGC TGC ACC TGC CCC TCG GGC TTC
 K   D   R   V   N   G   F   S   C   T   C   P   S   G   F
1577                1592                1607
AGC GGC TCC ACG TGT CAG CTG GAC GTG GAC GAA TGC GCC AGC ACG
 S   G   S   T   C   Q   L   D   V   D   E   C   A   S   T
1622                1637                1652
CCC TGC AGG AAT GGC GCC AAA TGC GTG GAC CAG CCC GAT GGC TAC
 P   C   R   N   G   A   K   C   V   D   Q   P   D   G   Y
1667                1682                1697
GAG TGC CGC TGT GCC GAG GGC TTT GAG GGC ACG CTG TGT GAT CGC
 E   C   R   C   A   E   G   F   E   G   T   L   C   D   R
1712                1727                1742
AAC GTG GAC GAC TGC TCC CCT GAC CCA TGC CAC CAT GGT CGC TGC
 N   V   D   D   C   S   P   D   P   C   H   H   G   R   C
1757                1772                1787
GTG GAT GGC ATC GCC AGC TTC TCA TGT GCC TGT GCT CCT GGC TAC
 V   D   G   I   A   S   F   S   C   A   C   A   P   G   Y
1802                1817                1832
ACG GGC ACA CGC TGC GAG AGC CAG GTG GAC GAA TGC GCC AGC CAG
 T   G   T   R   C   E   S   Q   V   D   E   C   R   S   Q
1847                1862                1877
CCC TGC CGC CAT GGC GGC AAA TGC CTA GAC CTG GTG GAC AAG TAC
 P   C   R   H   G   G   K   C   L   D   L   V   D   K   Y
1892                1907                1922
CTC TGC CGC TGC CCT TCT GGG ACC ACA GGT GTG AAC TGC GAA GTG
 L   C   R   C   P   S   G   T   T   G   V   N   C   E   V
1937                1952                1967
AAC ATT GAC GAC TGT GCC AGC AAC CCC TGC ACC TTT GGA GTC TGC
 N   I   D   D   C   A   S   N   P   C   T   F   G   V   C
1982                1997                2012
CGT GAT GGC ATC AAC CGC TAC GAC TGT GTC TGC CAA CCT GGC TTC
 R   D   G   I   N   R   Y   D   C   V   C   Q   P   G   F
2027                2042                2057
ACA GGG CCC CTT TGT AAC GTG GAG ATC AAT GAG TGT GCT TCC AGC
 T   G   P   L   C   N   V   E   I   N   E   C   A   S   S
```

FIG. 1B

```
     2072                    2087                    2102
CCA TGC GGC GAG GGA GGT TCC TGT GTG GAT GGG GAA AAT GGC TTC
 P   C   G   E   G   G   S   C   V   D   G   E   N   G   F
     2117                    2132                    2147
CGC TGC CTC TGC CCG CCT GGC TCC TTG CCC CCA CTC TGC CTC CCC
 R   C   L   C   P   P   G   S   L   P   P   L   C   L   P
     2162                    2177                    2192
CCG AGC CAT CCC TGT GCC CAT GAG CCC TGC AGT CAC GGC ATC TGC
 P   S   H   P   C   A   H   E   P   C   S   H   G   I   C
     2207                    2222                    2237
TAT GAT GCA CCT GGC GGG TTC CGC TGT GTG TGT GAG CCT GGC TGG
 Y   D   A   P   G   G   F   R   C   V   C   E   P   G   W
     2252                    2267                    2282
AGT GGC CCC CGC TGC AGC CAG AGC CTG GCC CGA GAC GCC TGT GAG
 S   G   P   R   C   S   Q   S   L   A   R   D   A   C   E
     2297                    2312                    2327
TCC CAG CCG TGC AGG GCC GGT GGG ACA TGC AGC AGC GAT GGA ATG
 S   Q   P   C   R   A   G   G   T   C   S   S   D   G   M
     2342                    2357                    2372
GGT TTC CAC TGC ACC TGC CCG CCT GGT GTC CAG GGA CGT CAG TGT
 G   F   H   C   T   C   P   P   G   V   Q   G   R   Q   C
     2387                    2402                    2417
GAA CTC CTC TCC CCC TGC ACC CCG AAC CCC TGT GAG CAT GGG GGC
 E   L   L   S   P   C   T   P   N   P   C   E   H   G   G
     2432                    2447                    2462
CGC TGC GAG TCT GCC CCT GGC CAG CTG CCT GTC TGC TCC TGC CCC
 R   C   E   S   A   P   G   Q   L   P   V   C   S   C   P
     2477                    2492                    2507
CAG GGC TGG CAA GGC CCA CGA TGC CAG CAG GAT GTG GAC GAG TGT
 Q   G   W   Q   G   P   R   C   Q   Q   D   V   D   E   C
     2522                    2537                    2552
GCT GGC CCC GCA CCC TGT GGC CCT CAT GGT ATC TGC ACC AAC CTG
 A   G   P   A   P   C   G   P   H   G   I   C   T   N   L
     2567                    2582                    2597
GCA GGG AGT TTC AGC TGC ACC TGC CAT GGA GGG TAC ACT GGC CCT
 A   G   S   F   S   C   T   C   H   G   G   Y   T   G   P
     2612                    2627                    2642
TCC TGT GAT CAG GAC ATC AAT GAC TGT GAC CCC AAC CCA TGC CTG
 S   C   D   Q   D   I   N   D   C   D   P   N   P   C   L
     2657                    2672                    2687
AAC GGT GGC TCG TGC CAA GAC GGC GTG GGC TCC TTT TCC TGC TCC
 N   G   G   S   C   Q   D   G   V   G   S   F   S   C   S
     2702                    2717                    1732
TGC CTC CCT GGT TTC GCC GGC CCA CGA TGC GCC CGC GAT GTG GAT
 C   L   P   G   F   A   G   P   R   C   A   R   D   V   D
     2747                    2762                    2777
GAG TGC CTG AGC AAC CCC TGC GGC CCG GGC ACC TGT ACC GAC CAC
 E   C   L   S   N   P   C   G   P   G   T   C   T   D   H
     2792                    2807                    2822
GTG GCC TCC TTC ACC TGC ACC TGC CCG CCG GGC TAC GGA GGC TTC
 V   A   S   F   T   C   T   C   P   P   G   Y   G   G   F
     2837                    2852                    2867
CAC TGC GAA CAG GAC CTG CCC GAC TGC AGC CCC AGC TCC TGC TTC
 H   C   E   Q   D   L   P   D   C   S   P   S   S   C   F
     2882                    2897                    2912
AAT GGC GGG ACC TGT GTG GAC GGC GTG AAC TCG TTC AGC TGC CTG
 N   G   G   T   C   V   D   G   V   N   S   F   S   C   L
     2927                    2942                    2957
TGC CGT CCC GGC TAC ACA GGA GCC CAC TGC CAA CAT GAG GCA GAC
 C   R   P   G   Y   T   G   A   H   C   Q   H   E   A   D
     2972                    2987                    3002
CCC TGC CTC TCG CGG CCC TGC CTA CAC GGG GGC GTC TGC AGC GCC
 P   C   L   S   R   P   C   L   H   G   G   V   C   S   A
     3017                    3032                    3047
GCC CAC CCT GGC TTC CGC TGT ACC TGC CTC GAG AGC TTC ACG GGC
 A   H   P   G   F   R   C   T   C   L   E   S   F   T   G
     3062                    3077                    3092
CCG CAG TGC CAG ACG CTG GTG GAT TGG TGC AGC CGC CAG CCT TGT
 P   Q   C   Q   T   L   V   D   W   C   S   R   Q   P   C
```

FIG. 1C

```
                3107                           3122                          3137
              CAA AAC GGG GGT CGC TGC GTC CAG ACT GGG GCC TAT TGC CTT TGT
               Q   N   G   G   R   C   V   Q   T   G   A   Y   C   L   C
                3152                           3167                          3182
              CCC CCT GGA TGG AGC GGA CGC CTC TGT GAC ATC CGA AGC TTG CCC
               P   P   G   W   S   G   R   L   C   D   I   R   S   L   P
                3197                           3212                          3227
              TGC AGG GAG GCC GCA GCC CAG ATC GGG GTG CGG CTG GAG CAG CTG
               C   R   E   A   A   A   Q   I   G   V   R   L   E   Q   L
                3242                           3257                          3272
              TGT CAG GCG GGT GGG CAG TGT GTG GAT GAA GAC AGC TCC CAC TAC
               C   Q   A   G   G   Q   C   V   D   E   D   S   S   H   Y
                3287                           3257                          3272
              TGC GTG TGC CCA GAG GGC CGT ACT GGT AGC CAC TGT GAG CAG GAG
               C   V   C   P   E   G   R   T   G   S   H   C   E   Q   E
                3332                           3347                          3362
              GTG GAC CCC TGC TTG GCC CAG CCC TGC CAG CAT GGG GGG ACC TGC
               V   D   P   C   L   A   Q   P   C   Q   H   G   G   T   C
                3377                           3392                          3407
              CGT GGC TAT ATG GGG GGC TAC ATG TGT GAG TGT CTT CCT GGC TAC
               R   G   Y   M   G   G   Y   M   C   E   C   L   P   G   Y
                3422                           3437                          3452
              AAT GGT GAT AAC TGT GAG GAC GAC GTG GAC GAG TGT GCC TCC CAG
               N   G   D   N   C   E   D   D   V   D   E   C   A   S   Q
                3467                           3482                          3497
              CCC TGC CAG CAC GGG GGT TCA TGC ATT GAC CTC GTG GCC CGC TAT
               P   C   Q   H   G   G   S   C   I   D   L   V   A   R   Y
                3512                           3527                          3542
              CTC TGC TCC TGT CCC CCA GGA ACG CTG GGG GTG CTC TGC GAG ATT
               L   C   S   C   P   P   G   T   L   G   V   L   C   E   I
                3557                           3572                          3587
              AAT GAG GAT GAC TGC GGC CCA GGC CCA CCG CTG GAC TCA GGG CCC
               N   E   D   D   C   G   P   G   P   P   L   D   S   G   P
                3602                           3617                          3632
              CGG TGC CTA CAC AAT GGC ACC TGC GTG GAC CTG GTG GGT GGT TTC
               R   C   L   H   N   G   T   C   V   D   L   V   G   G   F
                3647                           3662                          3672
              CGC TGC ACC TGT CCC CCA GGA TAC ACT GGT TTG CGC TGC GAG GCA
               R   C   T   C   P   P   G   Y   T   G   L   R   C   E   A
                3692                           3707                          3722
              GAC ATC AAT GAG TGT CGC TCA GGT GCC TGC CAC GCG GCA CAC ACC
               D   I   N   E   C   R   S   G   A   C   H   A   A   H   T
                3737                           3752                          3767
              CGG GAC TGC CTG CAG GAC CCA GGC GGA GGT TTC CGT TGC CTT TGT
               R   D   C   L   Q   D   P   G   G   G   F   R   C   L   C
                3782                           3797                          3812
              CAT GCT GGC TTC TCA GGT CCT CGC TGT CAG ACT GTC CTG TCT CCC
               H   A   G   F   S   G   P   R   C   Q   T   V   L   S   P
                3827                           3842                          3857
              TGC GAG TCC CAG CCA TGC CAG CAT GGA GGC CAG TGC CGT CCT AGC
               C   E   S   Q   P   C   Q   H   G   G   Q   C   R   P   S
                3872                           3887                          3902
              CCG GGT CCT GGG GGT GGG CTG ACC TTC ACC TGT CAC TGT GCC CAG
               P   G   P   G   G   G   L   T   F   T   C   H   C   A   Q
                3917                           3932                          3947
              CCG TTC TGG GGT CCG CGT TGC GAG CGG GTG GCG CGC TCC TGC CGG
               P   F   W   G   P   R   C   E   R   V   A   R   S   C   R
                3962                           3977                          3992
              GAG CTG CAG TGC CCG GTG GGC GTC CCA TGC CAG CAG ACG CCC CGC
               E   L   Q   C   P   V   G   V   P   C   Q   Q   T   P   R
                4007                           4022                          4037
              GGG CCG CGC TGC GCC TGC CCC CCA GGG TTG TCG GGA CCC TCC TGC
               G   P   R   C   A   C   P   P   G   L   S   G   P   S   C
                4052                           4067                          4082
              CGC AGC TTC CCG GGG TCG CCG CCG GGG GCC AGC AAC GCC AGC TGC
               R   S   F   P   G   S   P   P   G   A   S   N   A   S   C
                4097                           4112                          4127
              GCG GCC GCC CCC TGT CTC CAC GGG GGC TCC TGC CGC CCC GCG CCG
               A   A   A   P   C   L   H   G   G   S   C   R   P   A   P
```

FIG. 1D

```
                4142                    4157                    4172
             TTC GCG CCC TTC TTC CGC TGC GCT TGC GCG CAG GGC TGG ACC GGG
              L   A   P   F   F   R   C   A   C   A   Q   G   W   T   G
                4187                    4202                    4217
             CCG CGC TGC GAG GCG CCC GCC GCG GCA CCC GAG GTC TCG GAG GAG
              P   R   C   E   A   P   A   A   A   P   E   V   S   E   E
                4232                    4247                    4262
             CCG CGG TGC CCG CGC GCC GCC TGC CAG GCC AAG CGC GGG GAC CAG
              P   R   C   P   R   A   A   C   Q   A   K   R   G   D   Q
                4277                    4292                    4307
             CGC TGC GAC CGC GAG TGC AAC AGC CCA GGC TGC GGC TGG GAC GGC
              R   C   D   R   E   C   N   S   P   G   C   G   W   D   G
                4322                    4337                    4352
             GGC GAC TGC TCG CTG AGC GTG GGC GAC CCC TGG CGG CAA TGC GAG
              G   D   C   S   L   S   V   G   D   P   W   R   Q   C   E
                4367                    4382                    4397
             GCG CTG CAG TGC TGG CGC CTC TTC AAC AAC AGC CGC TGC GAC CCC
              A   L   Q   C   W   R   L   F   N   N   S   R   C   D   P
                4412                    4427                    4442
             GCC TGC AGC TCG CCC GCC TGC CTC TAC GAC AAC TTC GAC TGC CAC
              A   C   S   S   P   A   C   L   Y   D   N   F   D   C   H
                4457                    4472                    4487
             GCC GGT GGC CGC GAG CGC ACT TGC AAC CCG GTG TAC GAG AAG TAC
              A   G   G   R   E   R   T   C   N   P   V   Y   E   K   Y
                4502                    4517                    4532
             TGC GCC GAC CAC TTT GCC GAC GGC CGC TGC GAC CAG GGC TGC AAC
              C   A   D   H   F   A   D   G   R   C   D   Q   G   C   N
                4547                    4562                    4577
             ACG GAG GAG TGC GGC TGG GAT GGG CTG GAT TGT GCC AGC GAG GTG
              T   E   E   C   G   W   D   G   L   D   C   A   S   E   V
                4592                    4607                    4622
             CCG GCC CTG CTG GCC CGC GGC GTG CTG GTG CTC ACA GTG CTG CTG
              P   A   L   L   A   R   G   V   L   V   L   T   V   L   L
                4637                    4652                    4667
             CCG CCG GAG GAG CTA CTG CGT TCC AGC GCC GAC TTT CTG CAG CGC
              P   P   E   E   L   L   R   S   S   A   D   F   L   Q   R
                4682                    4697                    4712
             CTC AGC GCC ATC CTG CGC ACC TCG CTG CGC TTC CGC CTG GAC GCG
              L   S   A   I   L   R   T   S   L   R   F   R   L   D   A
                4727                    4742                    4757
             CAC GGC CAG GCC ATG GTC TTC CCT TAC CAC CGG CCT AGT CCT GGC
              H   G   Q   A   M   V   F   P   Y   H   R   P   S   P   G
                4772                    4787                    4802
             TCC GAA CCC CGG GCC CGT CGG GAG CTG GCC CCC GAG GTG ATC GGC
              S   E   P   R   A   R   R   E   L   A   P   E   V   I   G
                4817                    4832                    4847
             TCG GTA GTA ATG CTG GAG ATT GAC AAC CGG CTC TGC CTG CAG TCG
              S   V   V   M   L   E   I   D   N   R   L   C   L   Q   S
                4862                    4877                    4892
             CCT GAG AAT GAT CAC TGC TTC CCC GAT GCC CAG AGC GCC GCT GAC
              P   E   N   D   H   C   F   P   D   A   Q   S   A   A   D
                4907                    4922                    4937
             TAC CTG GGA GCG TTG TCA GCG GTG GAG CGC CTG GAC TTC CCG TAC
              Y   L   G   A   L   S   A   V   E   R   L   D   F   P   Y
                4952                    4967                    4982
             CCA CTG CGG GAC GTG CGG GGG GAG CCG CTG GAG CCT CCA GAA CCC
              P   L   R   D   V   R   G   E   P   L   E   P   P   E   P
                4997                    5012                    5027
             AGC GTC CCG CTG CTG CCA CTG CTA GTG GCG GGC GCT GTC TTG CTG
              S   V   P   L   L   P   L   L   V   A   G   A   V   L   L
                5042                    5057                    5072
             CTG GTC ATT CTC GTC CTG GGT GTC ATG GTG GCC CGG CGC AAG CGC
              L   V   I   L   V   L   G   V   M   V   A   R   R   K   R
                5087                    5102                    5117
             GAG CAC AGC ACC CTC TGG TTC CCT GAG GGC TTC TCA CTG CAC AAG
              E   H   S   T   L   W   F   P   E   G   F   S   L   H   K
                5132                    5147                    5162
             GAC GTG GCC TCT GGT CAC AAG GGC CGG CGG GAA CCC GTG GGC CAG
              D   V   A   S   G   H   K   G   R   R   E   P   V   G   Q
```

FIG. 1E

```
      5177                  5192                     5207
GAC GCG CTG GGC ATG AAG AAC ATG GCC AAG GGT GAG AGC CTG ATG
 D   A   L   G   M   K   N   M   A   K   G   E   S   L   M
      5222                  5237                     5252
GGG GAG GTG GCC ACA GAC TGG ATG GAC ACA GAG TGC CCA GAG GCC
 G   E   V   A   T   D   W   M   D   T   E   C   P   E   A
      5267                  5282                     5297
AAG CGG CTA AAG GTA GAG GAG CCA GGC ATG GGG GCT GAG GAG GCT
 K   R   L   K   V   E   E   P   G   M   G   A   E   E   A
      5312                  5327                     5342
GTG GAT TGC CGT CAG TGG ACT CAA CAC CAT CTG GTT GCT GCT GAC
 V   D   C   R   Q   W   T   Q   H   H   L   V   A   A   D
      5357                  5372                     5387
ATC CGC GTG GCA CCA GCC ATG GCA CTG ACA CCA CCA CAG GGC GAC
 I   R   V   A   P   A   M   A   L   T   P   P   Q   G   D
      5402                  5417                     5432
GCA GAT GCT GAT GGC ATG GAT GTC AAT GTG CGT GGC CCA GAT GGC
 A   D   A   D   G   M   D   V   N   V   R   G   P   D   G
      5447                  5462                     5477
TTC ACC CCG CTA ATG CTG GCT TCC TTC TGT GGG GGG GCT CTG GAG
 F   T   P   L   M   L   A   S   F   C   G   G   A   L   E
      5492                  5507                     5522
CCA ATG CCA ACT GAA GAG GAT GAG GCA GAT GAC ACA TCA GCT AGC
 P   M   P   T   E   E   D   E   A   D   D   T   S   A   S
      5537                  5552                     5567
ATC ATC TCC GAC CTG ATC TGC CAG GGG GCT CAG CTT GGG GCA CGG
 I   I   S   D   L   I   C   Q   G   A   Q   L   G   A   R
      5582                  5597                     5612
ACT GAC CGT ACT GGC GAG ACT GCT TTG CAC CTG GCT GCC CGT TAT
 T   D   R   T   G   E   T   A   L   H   L   A   A   R   Y
      5627                  5642                     5657
GCC CGT GCT GAT GCA GCC AAG CGG CTG CTG GAT GCT GGG GCA GAC
 A   R   A   D   A   A   K   R   L   L   D   A   G   A   D
      5672                  5687                     5702
ACC AAT GCC CAG GAC CAC TCA GGC CGC ACT CCC CTG CAC ACA GCT
 T   N   A   Q   D   H   S   G   R   T   P   L   H   T   A
      5717                  5732                     5747
GTC ACA GCC GAT GCC CAG GGT GTC TTC CAG ATT CTC ATC CGA AAC
 V   T   A   D   A   Q   G   V   F   Q   I   L   I   R   N
      5762                  5777                     5792
CGC TCT ACA GAC TTG GAT GCC CGC ATG GCA GAT GGC TCA ACG GCA
 R   S   T   D   L   D   A   R   M   A   D   G   S   T   A
      5807                  5822                     5837
CTG ATC CTG GCG GCC CGC CTG GCA GTA GAG GGC ATG GTG GAA GAG
 L   I   L   A   A   R   L   A   V   E   G   M   V   E   E
      5852                  5867                     5882
CTC ATC GCC AGC CAT GCT GAT GTC AAT GCT GTG GAT GAG CTT GGG
 L   I   A   S   H   A   D   V   N   A   V   D   E   L   G
      5897                  5912                     5927
AAA TCA GCC TTA CAC TGG GCT GCG GCT GTG AAC AAC GTG GAA GCC
 K   S   A   L   H   W   A   A   A   V   N   N   V   E   A
      5942                  5957                     5972
ACT TTG GCC CTG CTC AAA AAT GGA GCC AAT AAG GAC ATG CAG GAT
 T   L   A   L   L   K   N   G   A   N   K   D   M   Q   D
      5987                  6002                     6017
AGC AAG GAG GAG ACC CCC CTA TTC CTG GCC GCC CGC GAG GGC AGC
 S   K   E   E   T   P   L   F   L   A   A   R   E   G   S
      6032                  6047                     6062
TAT GAG GCT GCC AAG CTG CTG TTC GAC CAC TTT GCC AAC CGT GAG
 Y   E   A   A   K   L   L   F   D   H   F   A   N   R   E
      6077                  6092                     6107
ATC ACC GAC CAC CTG GAC AGG CTG CCG CGG GAC GTA GCC CAG GAG
 I   T   D   H   L   D   R   L   P   R   D   V   A   Q   E
      6122                  6137                     6152
AGA CTG CAC CAG GAC ATC GTG CGC TTG CTG GAT CAA CCC AGT GGG
 R   L   H   Q   D   I   V   R   L   L   D   Q   P   S   G
      6167                  6182                     6197
CCC CGC AGC CCC CCC GGT CCC CAC GGC CTG GGG CCT CTG CTC TGT
 P   R   S   P   P   G   P   H   G   L   G   P   L   L   C
```

FIG. 1F

```
6212                    6227                    6242
CCT CCA GGG GCC TTC CTC CCT GGC CTC AAA GCG GCA CAG TCG GGG
 P   P   G   A   F   L   P   G   L   K   A   A   Q   S   G
     6257                    6272                    6287
TCC AAG AAG AGC AGG AGG CCC CCC GGG AAG GCG GGG CTG GGG CCG
 S   K   K   S   R   R   P   P   G   K   A   G   L   G   P
6302                    6317                    6332
CAG GGG CCC CGG GGG CGG GGC AAG AAG CTG ACG CTG GCC TGC CCG
 Q   G   P   R   G   R   G   K   K   L   T   L   A   C   P
6347                    6362                    6377
GGC CCC CTG GCT GAC AGC TCG GTC ACG CTG TCG CCC GTG GAC TCG
 G   P   L   A   D   S   S   V   T   L   S   P   V   D   S
6392                    6407                    6422
CTG GAC TCC CCG CGG CCT TTC GGT GGG CCC CCT GCT TCC CCT GGT
 L   D   S   P   R   P   F   G   G   P   P   A   S   P   G
6437                    6452                    6467
GGC TTC CCC CTT GAG GGG CCC TAT GCA GCT GCC ACT GCC ACT GCA
 G   F   P   L   E   G   P   Y   A   A   A   T   A   T   A
6482                    6497                    6512
GTG TCT CTG GCA CAG CTT GGT GGC CCA GGC CGG GCA GGT CTA GGG
 V   S   L   A   Q   L   G   G   P   G   R   A   G   L   G
6527                    6542                    6557
CGC CAG CCC CCT GGA GGA TGT GTA CTC AGC CTG GGC CTG CTG AAC
 R   Q   P   P   G   G   C   V   L   S   L   G   L   L   N
6572                    6587                    6602
CCT GTG GCT GTG CCC CTC GAT TGG GCC CGG CTG CCC CCA CCT GCC
 P   V   A   V   P   L   D   W   A   R   L   P   P   P   A
6617                    6632                    6647
CCT CCA GGC CCC TCG TTC CTG CTG CCA CTG GCG CCG GGA CCC CAG
 P   P   G   P   S   F   L   L   P   L   A   P   G   P   Q
6662                    6677                    6692
CTG CTC AAC CCA GGG ACC CCC GTC TCC CCG CAG GAG CGG CCC CCG
 L   L   N   P   G   T   P   V   S   P   Q   E   R   P   P
6707                    6722                    6737
CCT TAC CTG GCA GTC CCA GGA CAT GGC GAG GAG TAC CCG GTG GCT
 P   Y   L   A   V   P   G   H   G   E   E   Y   P   V   A
6752                    6767                    6782
GGG GCA CAC AGC AGC CCC CCA AAG GCC CGC TTC CTG CGG GTT CCC
 G   A   H   S   S   P   P   K   A   R   F   L   R   V   P
6797                    6812                    6827
AGT GAG CAC CCT TAC CTG ACC CCA TCC CCC GAA TCC CCT GAG CAC
 S   E   H   P   Y   L   T   P   S   P   E   S   P   E   H
6842                    6857                    6872
TGG GCC AGC CCC TCA CCT CCC TCC CTC TCA GAC TGG TCC GAA TCC
 W   A   S   P   S   P   P   S   L   S   D   W   S   E   S
6887                    6902                    6917
ACG CCT AGC CCA GCC ACT GCC ACT GGG GCC ATG GCC ACC ACC ACT
 T   P   S   P   A   T   A   T   G   A   M   A   T   T   T
6932                    6947                    6962
GGG GCA CTG CCT GCC CAG CCA CTT CCC TTG TCT GTT CCC AGC TCC
 G   A   L   P   A   Q   P   L   P   L   S   V   P   S   S
6977                    6992                    7007
CTT GCT CAG GCC CAG ACC CAG CTG GGG CCC CAG CCG GAA GTT ACC
 L   A   Q   A   Q   T   Q   L   G   P   Q   P   E   V   T
7022                    7037                    7052
CCC AAG AGG CAA GTG TTG GCC TGA GAC GCT CGT CAG TTC TTA GAT
 P   K   R   Q   V   L   A   *                  (SEQ ID NO:2)
7067                    7082                    7097
CTT GGG GGC CTA AAG AGA CCC CCG TCC TGC CTC CTT TCT TTC TCT 7112                    7127                    7142
GTC TCT TCC TTC CTT TTA GTC TTT TTC ATC CTC TTC TCT TTC CAC 7157                    7172                    7187
CAA CCC TCC TGC ATC CTT GCC TTG CAG CGT GAC CGA GAT AGG TCA 7202                    7217                    7232
TCA GCC CAG GGC TTC AGT CTT CCT TTA TTT ATA ATG GGT GGG GGC 7247                    7262                    7277
```

FIG. 1G

```
                TAC CAC CCA CCC TCT CAG TCT TGT GAA GAG TCT GGG ACC TCC TTC
         7292              7307              7322
         TTC CCC ACT TCT CTC TTC CCT CAT TCC TTT CTC TCT CCT TCT GGC
         7337              7352              7367
         CTC TCA TTT CCT TAC ACT CTG ACA TGA ATG AAT TAT TAT TAT TTT
         7382              7397              7412
         TCT TTT TCT TTT TTT TTT TAC ATT TTG TAT AGA AAC AAA TTC ATT
         7427              7442              7457
         TAA ACA AAC TTA TTA TTA TTA TTT TTT ACA AAA TAT ATA TAT GGA
         7472              7487              7502
         GAT GCT CCC TCC CCC TGT GAA CCC CCC AGT GCC CCC GTG GGG CTG
         7517              7532              7547
         AGT CTG TGG GCC CAT TCG GCC AAG CTG GAT TCT GTG TAC CTA GTA
         7562              7577              7592
         CAC AGG CAT GAC TGG GAT CCC GTG TAC CGA GTA CAC GAC CCA GGT
         7607              7622              7637
         ATG TAC CAA GTA GGC ACC CTT GGG CGC ACC CAC TGG GGC CAG GGG
         7652              7667              7682
         TCG GGG GAG TGT TGG GAG CCT CCT CCC CAC CCC ACC TCC CTC ACT
         7697              7712              7727
         TCA CTG CAT TCC AGA TTG GAC ATG TTC CAT AGC CTT GCT GGG GAA
         7742              7757              7772
         GGG CCC ACT GCC AAC TCC CTC TGC CCC AGC CCC ACC CTT GGC CAT
         7787              7802              7817
         CTC CCT TTG GGA ACT AGG GGG CTG CTG GTG GGA AAT GGG AGC CAG
         7832              7847              7862
         GGC AGA TGT ATG CAT TCC TTT ATG TCC CTG TAA ATG TGG GAC TAC
         7877              7892              7907
         AAG AAG AGG AGC TGC CTG AGT GGT ACT TTC TCT TCC TGG TAA TCC
         7922              7937              7952
         TCT GGC CCA GCC TTA TGG CAG AAT AGA GGT ATT TTT AGG CTA TTT
         7967              7982              7997
         TTG TAA TAT GGC TTC TGG TCA AAA TCC CTG TGT AGC TGA ATT CCC
         8012              8027              8042
         AAG CCC TGC ATT GTA CAG CCC CCC ACT CCC CTC ACC ACC TAA TAA
         8057              8072
         AGG AAT AGT TAA CAC TCA AAA AAA AAA AAA AAA AAA              (SEQ ID NO:1)
```

FIG. 1H

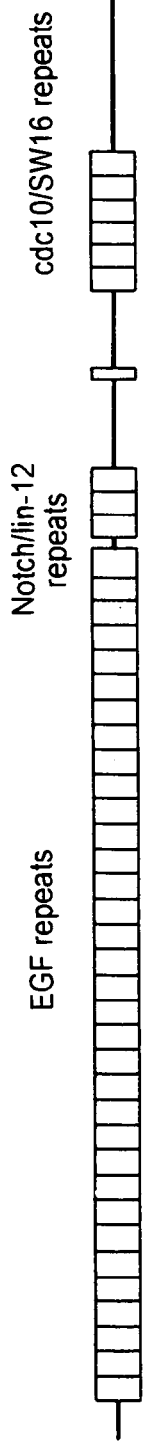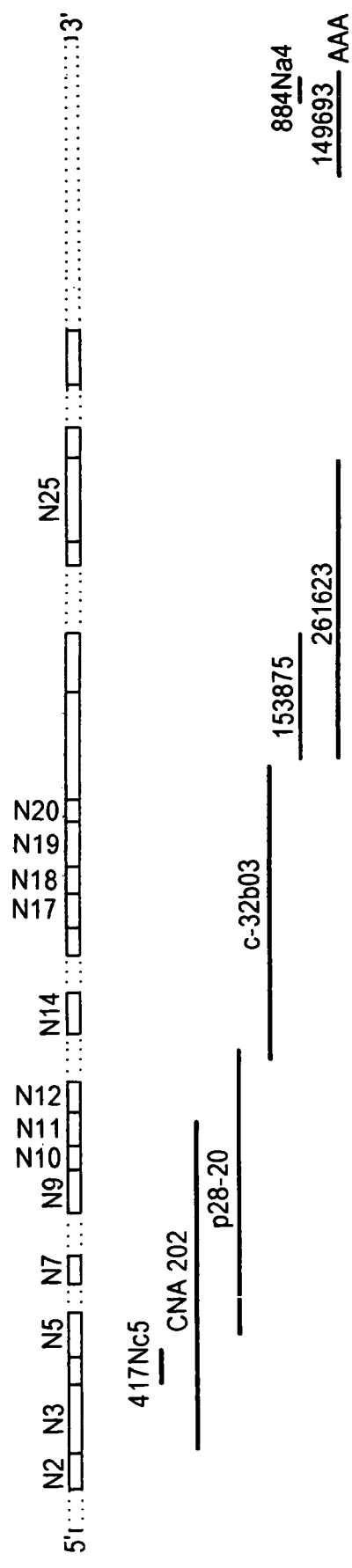
FIG. 2A
FIG. 2B

SEQUENCE LISTING

```
<160> NUMBER OF SEQ ID NOS: 163

<210> SEQ ID NO 1
<211> LENGTH: 8091
<212> TYPE: DNA
<213> ORGANISM: Homo sapiens
<220> FEATURE:
<221> NAME/KEY: CDS
<222> LOCATION: (79)..(7041)
<223> OTHER INFORMATION: human ADNc Notch 3

<400> SEQUENCE: 1
acgcggcgcg gaggctggcc cgggacgcgc ccggagccca gggaaggagg gaggagggga        60
gggtcgcggc cggccgcc atg ggg ccg ggg gcc cgt ggc cgc cgc cgc cgc       111
                    Met Gly Pro Gly Ala Arg Gly Arg Arg Arg Arg
                    1               5                   10 cgt cgc ccg atg tcg ccg cca ccg cca ccg cca ccc gtg cgg gcg ctg       159
Arg Arg Pro Met Ser Pro Pro Pro Pro Pro Pro Val Arg Ala Leu
            15                  20                  25 ccc ctg ctg ctg ctg cta gcg ggg ccg ggg gct gca gcc ccc cct tgc       207
Pro Leu Leu Leu Leu Leu Ala Gly Pro Gly Ala Ala Ala Pro Pro Cys
        30                  35                  40 ctg gac gga agc ccg tgt gca aat gga ggt cgt tgc acc cag ctg ccc       255
Leu Asp Gly Ser Pro Cys Ala Asn Gly Gly Arg Cys Thr Gln Leu Pro
    45                  50                  55 tcc cgg gag gct gcc tgc ctg tgc ccg cct ggc tgg gtg ggt gag cgg       303
Ser Arg Glu Ala Ala Cys Leu Cys Pro Pro Gly Trp Val Gly Glu Arg
60                  65                  70                  75 tgt cag ctg gag gac ccc tgt cac tca ggc ccc tgt gct ggc cgt ggt       351
Cys Gln Leu Glu Asp Pro Cys His Ser Gly Pro Cys Ala Gly Arg Gly
                80                  85                  90 gtc tgc cag agt tca gtg gtg gct ggc acc gcc cga ttc tca tgc cgg       399
Val Cys Gln Ser Ser Val Val Ala Gly Thr Ala Arg Phe Ser Cys Arg
            95                  100                 105 tgc ccc cgt ggc ttc cga ggc cct gac tgc tcc ctg cca gat ccc tgc       447
Cys Pro Arg Gly Phe Arg Gly Pro Asp Cys Ser Leu Pro Asp Pro Cys
        110                 115                 120 ctc agc agc cct tgt gcc cac ggt gcc cgc tgc tca gtg ggg ccc gat       495
Leu Ser Ser Pro Cys Ala His Gly Ala Arg Cys Ser Val Gly Pro Asp
    125                 130                 135 gga cgc ttc ctc tgc tcc tgc cca cct ggc tac cag ggc cgc agc tgc       543
Gly Arg Phe Leu Cys Ser Cys Pro Pro Gly Tyr Gln Gly Arg Ser Cys
140                 145                 150                 155
```

-continued

| | |
|---|---|
| cga agc gac gtg gat gag tgc cgg gtg ggt gag ccc tgc cgc cat ggt<br>Arg Ser Asp Val Asp Glu Cys Arg Val Gly Glu Pro Cys Arg His Gly<br>                160                     165                   170 | 591 |
| ggc acc tgc ctc aac aca cct ggc tcc ttc cgc tgc cag tgt cca gct<br>Gly Thr Cys Leu Asn Thr Pro Gly Ser Phe Arg Cys Gln Cys Pro Ala<br>             175                    180                      185 | 639 |
| ggc tac aca ggg cca cta tgt gag aac ccc gcg gtg ccc tgt gcg ccc<br>Gly Tyr Thr Gly Pro Leu Cys Glu Asn Pro Ala Val Pro Cys Ala Pro<br>         190                    195                    200 | 687 |
| tca cca tgc cgt aac ggg ggc acc tgc agg cag agt ggc gac ctc act<br>Ser Pro Cys Arg Asn Gly Gly Thr Cys Arg Gln Ser Gly Asp Leu Thr<br>205                    210                    215 | 735 |
| tac gac tgt gcc tgt ctt cct ggg ttt gag ggt cag aat tgt gaa gtg<br>Tyr Asp Cys Ala Cys Leu Pro Gly Phe Glu Gly Gln Asn Cys Glu Val<br>220                    225                    230                    235 | 783 |
| aac gtg gac gac tgt cca gga cac cga tgt ctc aat ggg ggg aca tgc<br>Asn Val Asp Asp Cys Pro Gly His Arg Cys Leu Asn Gly Gly Thr Cys<br>                  240                    245                    250 | 831 |
| gtg gat ggc gtc aac acc tat aac tgc cag tgc cct cct gag tgg aca<br>Val Asp Gly Val Asn Thr Tyr Asn Cys Gln Cys Pro Pro Glu Trp Thr<br>             255                    260                    265 | 879 |
| ggc cag ttc tgc acg gag gac gtg gat gag tgt cag ctg cag ccc aac<br>Gly Gln Phe Cys Thr Glu Asp Val Asp Glu Cys Gln Leu Gln Pro Asn<br>         270                    275                    280 | 927 |
| gcc tgc cac aat ggg ggt acc tgc ttc aac acg ctg ggt ggc cac agc<br>Ala Cys His Asn Gly Gly Thr Cys Phe Asn Thr Leu Gly Gly His Ser<br>             285                    290                    295 | 975 |
| tgc gtg tgt gtc aat ggc tgg aca ggt gag agc tgc agt cag aat atc<br>Cys Val Cys Val Asn Gly Trp Thr Gly Glu Ser Cys Ser Gln Asn Ile<br>300                    305                    310                    315 | 1023 |
| gat gac tgt gcc aca gcc gtg tgc ttc cat ggg gcc acc tgc cat gac<br>Asp Asp Cys Ala Thr Ala Val Cys Phe His Gly Ala Thr Cys His Asp<br>                  320                    325                    330 | 1071 |
| cgc gtg gct tct ttc tac tgt gcc tgc ccc atg ggc aag act ggc ctc<br>Arg Val Ala Ser Phe Tyr Cys Ala Cys Pro Met Gly Lys Thr Gly Leu<br>             335                    340                    345 | 1119 |
| ctg tgt cac ctg gat gac gcc tgt gtc agc aac ccc tgc cac gag gat<br>Leu Cys His Leu Asp Asp Ala Cys Val Ser Asn Pro Cys His Glu Asp<br>         350                    355                    360 | 1167 |
| gct atc tgt gac aca aat ccg gtg aac ggc cgg gcc att tgc acc tgt<br>Ala Ile Cys Asp Thr Asn Pro Val Asn Gly Arg Ala Ile Cys Thr Cys<br>365                    370                    375 | 1215 |
| cct ccc ggc ttc acg ggt ggg gca tgt gac cag gat gtg gac gag tgc<br>Pro Pro Gly Phe Thr Gly Gly Ala Cys Asp Gln Asp Val Asp Glu Cys<br>380                    385                    390                    395 | 1263 |
| tct atc ggc gcc aac ccc tgc gag cac ttg ggc agg tgc gtg aac acg<br>Ser Ile Gly Ala Asn Pro Cys Glu His Leu Gly Arg Cys Val Asn Thr<br>                  400                    405                    410 | 1311 |
| cag ggc tcc ttc ctg tgc cag tgc ggt cgt ggc tac act gga cct cgc<br>Gln Gly Ser Phe Leu Cys Gln Cys Gly Arg Gly Tyr Thr Gly Pro Arg<br>             415                    420                    425 | 1359 |
| tgt gag acc gat gtc aac gag tgt ctg tcg ggg ccc tgc cga aac cag<br>Cys Glu Thr Asp Val Asn Glu Cys Leu Ser Gly Pro Cys Arg Asn Gln<br>                  430                    435                    440 | 1407 |
| gcc acg tgc ctc gac cgc ata ggc cag ttc acc tgt atc tgt atg gca<br>Ala Thr Cys Leu Asp Arg Ile Gly Gln Phe Thr Cys Ile Cys Met Ala<br>         445                    450                    455 | 1455 |
| ggc ttc aca gga acc tat tgc gag gtg gac att gac gag tgt cag agt<br>Gly Phe Thr Gly Thr Tyr Cys Glu Val Asp Ile Asp Glu Cys Gln Ser<br>460                    465                    470                    475 | 1503 |

```
agc ccc tgt gtc aac ggt ggg gtc tgc aag gac cga gtc aat ggc ttc      1551
Ser Pro Cys Val Asn Gly Gly Val Cys Lys Asp Arg Val Asn Gly Phe
            480                 485                 490 agc tgc acc tgc ccc tcg ggc ttc agc ggc tcc acg tgt cag ctg gac      1599
Ser Cys Thr Cys Pro Ser Gly Phe Ser Gly Ser Thr Cys Gln Leu Asp
        495                 500                 505 gtg gac gaa tgc gcc agc acg ccc tgc agg aat ggc gcc aaa tgc gtg      1647
Val Asp Glu Cys Ala Ser Thr Pro Cys Arg Asn Gly Ala Lys Cys Val
    510                 515                 520 gac cag ccc gat ggc tac gag tgc cgc tgt gcc gag ggc ttt gag ggc      1695
Asp Gln Pro Asp Gly Tyr Glu Cys Arg Cys Ala Glu Gly Phe Glu Gly
525                 530                 535 acg ctg tgt gat cgc aac gtg gac gac tgc tcc cct gac cca tgc cac      1743
Thr Leu Cys Asp Arg Asn Val Asp Asp Cys Ser Pro Asp Pro Cys His
540                 545                 550                 555 cat ggt cgc tgc gtg gat ggc atc gcc agc ttc tca tgt gcc tgt gct      1791
His Gly Arg Cys Val Asp Gly Ile Ala Ser Phe Ser Cys Ala Cys Ala
            560                 565                 570 cct ggc tac acg ggc aca cgc tgc gag agc cag gtg gac gaa tgc cgc      1839
Pro Gly Tyr Thr Gly Thr Arg Cys Glu Ser Gln Val Asp Glu Cys Arg
        575                 580                 585 agc cag ccc tgc cgc cat ggc ggc aaa tgc cta gac ctg gtg gac aag      1887
Ser Gln Pro Cys Arg His Gly Gly Lys Cys Leu Asp Leu Val Asp Lys
    590                 595                 600 tac ctc tgc cgc tgc cct tct ggg acc aca ggt gtg aac tgc gaa gtg      1935
Tyr Leu Cys Arg Cys Pro Ser Gly Thr Thr Gly Val Asn Cys Glu Val
605                 610                 615 aac att gac gac tgt gcc agc aac ccc tgc acc ttt gga gtc tgc cgt      1983
Asn Ile Asp Asp Cys Ala Ser Asn Pro Cys Thr Phe Gly Val Cys Arg
620                 625                 630                 635 gat ggc atc aac cgc tac gac tgt gtc tgc caa cct ggc ttc aca ggg      2031
Asp Gly Ile Asn Arg Tyr Asp Cys Val Cys Gln Pro Gly Phe Thr Gly
            640                 645                 650 ccc ctt tgt aac gtg gag atc aat gag tgt gct tcc agc cca tgc ggc      2079
Pro Leu Cys Asn Val Glu Ile Asn Glu Cys Ala Ser Ser Pro Cys Gly
        655                 660                 665 gag gga ggt tcc tgt gtg gat ggg gaa aat ggc ttc cgc tgc ctc tgc      2127
Glu Gly Gly Ser Cys Val Asp Gly Glu Asn Gly Phe Arg Cys Leu Cys
    670                 675                 680 ccg cct ggc tcc ttg ccc cca ctc tgc ctc ccc ccg agc cat ccc tgt      2175
Pro Pro Gly Ser Leu Pro Pro Leu Cys Leu Pro Pro Ser His Pro Cys
685                 690                 695 gcc cat gag ccc tgc agt cac ggc atc tgc tat gat gca cct ggc ggg      2223
Ala His Glu Pro Cys Ser His Gly Ile Cys Tyr Asp Ala Pro Gly Gly
700                 705                 710                 715 ttc cgc tgt gtg tgt gag cct ggc tgg agt ggc ccc cgc tgc agc cag      2271
Phe Arg Cys Val Cys Glu Pro Gly Trp Ser Gly Pro Arg Cys Ser Gln
            720                 725                 730 agc ctg gcc cga gac gcc tgt gag tcc cag ccg tgc agg gcc ggt ggg      2319
Ser Leu Ala Arg Asp Ala Cys Glu Ser Gln Pro Cys Arg Ala Gly Gly
        735                 740                 745 aca tgc agc agc gat gga atg ggt ttc cac tgc acc tgc ccg cct ggt      2367
Thr Cys Ser Ser Asp Gly Met Gly Phe His Cys Thr Cys Pro Pro Gly
    750                 755                 760 gtc cag gga cgt cag tgt gaa ctc ctc tcc ccc tgc acc ccg aac ccc      2415
Val Gln Gly Arg Gln Cys Glu Leu Leu Ser Pro Cys Thr Pro Asn Pro
765                 770                 775 tgt gag cat ggg ggc cgc tgc gag tct gcc cct ggc cag ctg cct gtc      2463
Cys Glu His Gly Gly Arg Cys Glu Ser Ala Pro Gly Gln Leu Pro Val
780                 785                 790                 795
```

```
tgc tcc tgc ccc cag ggc tgg caa ggc cca cga tgc cag cag gat gtg    2511
Cys Ser Cys Pro Gln Gly Trp Gln Gly Pro Arg Cys Gln Gln Asp Val
            800                 805                 810 gac gag tgt gct ggc ccc gca ccc tgt ggc cct cat ggt atc tgc acc    2559
Asp Glu Cys Ala Gly Pro Ala Pro Cys Gly Pro His Gly Ile Cys Thr
        815                 820                 825 aac ctg gca ggg agt ttc agc tgc acc tgc cat gga ggg tac act ggc    2607
Asn Leu Ala Gly Ser Phe Ser Cys Thr Cys His Gly Gly Tyr Thr Gly
830                 835                 840 cct tcc tgt gat cag gac atc aat gac tgt gac ccc aac cca tgc ctg    2655
Pro Ser Cys Asp Gln Asp Ile Asn Asp Cys Asp Pro Asn Pro Cys Leu
    845                 850                 855 aac ggt ggc tcg tgc caa gac ggc gtg ggc tcc ttt tcc tgc tcc tgc    2703
Asn Gly Gly Ser Cys Gln Asp Gly Val Gly Ser Phe Ser Cys Ser Cys
860                 865                 870                 875 ctc cct ggt ttc gcc ggc cca cga tgc gcc cgc gat gtg gat gag tgc    2751
Leu Pro Gly Phe Ala Gly Pro Arg Cys Ala Arg Asp Val Asp Glu Cys
                880                 885                 890 ctg agc aac ccc tgc ggc ccg ggc acc tgt acc gac cac gtg gcc tcc    2799
Leu Ser Asn Pro Cys Gly Pro Gly Thr Cys Thr Asp His Val Ala Ser
        895                 900                 905 ttc acc tgc acc tgc ccg ccg ggc tac gga ggc ttc cac tgc gaa cag    2847
Phe Thr Cys Thr Cys Pro Pro Gly Tyr Gly Gly Phe His Cys Glu Gln
    910                 915                 920 gac ctg ccc gac tgc agc ccc agc tcc tgc ttc aat ggc ggg acc tgt    2895
Asp Leu Pro Asp Cys Ser Pro Ser Ser Cys Phe Asn Gly Gly Thr Cys
925                 930                 935 gtg gac ggc gtg aac tcg ttc agc tgc ctg tgc cgt ccc ggc tac aca    2943
Val Asp Gly Val Asn Ser Phe Ser Cys Leu Cys Arg Pro Gly Tyr Thr
940                 945                 950                 955 gga gcc cac tgc caa cat gag gca gac ccc tgc ctc tcg cgg ccc tgc    2991
Gly Ala His Cys Gln His Glu Ala Asp Pro Cys Leu Ser Arg Pro Cys
                960                 965                 970 cta cac ggg ggc gtc tgc agc gcc gcc cac cct ggc ttc cgc tgc acc    3039
Leu His Gly Gly Val Cys Ser Ala Ala His Pro Gly Phe Arg Cys Thr
        975                 980                 985 tgc ctc gag agc ttc acg ggc ccg cag tgc cag acg ctg gtg gat tgg    3087
Cys Leu Glu Ser Phe Thr Gly Pro Gln Cys Gln Thr Leu Val Asp Trp
    990                 995                 1000 tgc agc cgc cag cct tgt caa aac ggg ggt cgc tgc gtc cag act ggg    3135
Cys Ser Arg Gln Pro Cys Gln Asn Gly Gly Arg Cys Val Gln Thr Gly
1005                1010                1015 gcc tat tgc ctt tgt ccc cct gga tgg agc gga cgc ctc tgt gac atc    3183
Ala Tyr Cys Leu Cys Pro Pro Gly Trp Ser Gly Arg Leu Cys Asp Ile
1020                1025                1030                1035 cga agc ttg ccc tgc agg gag gcc gca gcc cag atc ggg gtg cgg ctg    3231
Arg Ser Leu Pro Cys Arg Glu Ala Ala Ala Gln Ile Gly Val Arg Leu
                1040                1045                1050 gag cag ctg tgt cag gcg ggt ggg cag tgt gtg gat gaa gac agc tcc    3279
Glu Gln Leu Cys Gln Ala Gly Gly Gln Cys Val Asp Glu Asp Ser Ser
        1055                1060                1065 cac tac tgc gtg tgc cca gag ggc cgt act ggt agc cac tgt gag cag    3327
His Tyr Cys Val Cys Pro Glu Gly Arg Thr Gly Ser His Cys Glu Gln
    1070                1075                1080 gag gtg gac ccc tgc ttg gcc cag ccc tgc cag cat ggg ggg acc tgc    3375
Glu Val Asp Pro Cys Leu Ala Gln Pro Cys Gln His Gly Gly Thr Cys
1085                1090                1095 cgt ggc tat atg ggg ggc tac atg tgt gag tgt ctt cct ggc tac aat    3423
Arg Gly Tyr Met Gly Gly Tyr Met Cys Glu Cys Leu Pro Gly Tyr Asn
1100                1105                1110                1115
```

-continued

| | |
|---|---|
| ggt gat aac tgt gag gac gac gtg gac gag tgt gcc tcc cag ccc tgc<br>Gly Asp Asn Cys Glu Asp Asp Val Asp Glu Cys Ala Ser Gln Pro Cys<br>1120                      1125                    1130 | 3471 |
| cag cac ggg ggt tca tgc att gac ctc gtg gcc cgc tat ctc tgc tcc<br>Gln His Gly Gly Ser Cys Ile Asp Leu Val Ala Arg Tyr Leu Cys Ser<br>      1135                  1140                    1145 | 3519 |
| tgt ccc cca gga acg ctg ggg gtg ctc tgc gag att aat gag gat gac<br>Cys Pro Pro Gly Thr Leu Gly Val Leu Cys Glu Ile Asn Glu Asp Asp<br>1150                      1155                    1160 | 3567 |
| tgc ggc cca ggc cca ccg ctg gac tca ggg ccc cgg tgc cta cac aat<br>Cys Gly Pro Gly Pro Pro Leu Asp Ser Gly Pro Arg Cys Leu His Asn<br>      1165                  1170                    1175 | 3615 |
| ggc acc tgc gtg gac ctg gtg ggt ggt ttc cgc tgc acc tgt ccc cca<br>Gly Thr Cys Val Asp Leu Val Gly Gly Phe Arg Cys Thr Cys Pro Pro<br>1180                      1185                    1190                    1195 | 3663 |
| gga tac act ggt ttg cgc tgc gag gca gac atc aat gag tgt cgc tca<br>Gly Tyr Thr Gly Leu Arg Cys Glu Ala Asp Ile Asn Glu Cys Arg Ser<br>                1200                    1205                    1210 | 3711 |
| ggt gcc tgc cac gcg gca cac acc cgg gac tgc ctg cag gac cca ggc<br>Gly Ala Cys His Ala Ala His Thr Arg Asp Cys Leu Gln Asp Pro Gly<br>      1215                  1220                    1225 | 3759 |
| gga ggt ttc cgt tgc ctt tgt cat gct ggc ttc tca ggt cct cgc tgt<br>Gly Gly Phe Arg Cys Leu Cys His Ala Gly Phe Ser Gly Pro Arg Cys<br>1230                      1235                    1240 | 3807 |
| cag act gtc ctg tct ccc tgc gag tcc cag cca tgc cag cat gga ggc<br>Gln Thr Val Leu Ser Pro Cys Glu Ser Gln Pro Cys Gln His Gly Gly<br>      1245                  1250                    1255 | 3855 |
| cag tgc cgt cct agc ccg ggt cct ggg ggt ggg ctg acc ttc acc tgt<br>Gln Cys Arg Pro Ser Pro Gly Pro Gly Gly Gly Leu Thr Phe Thr Cys<br>1260                      1265                    1270                    1275 | 3903 |
| cac tgt gcc cag ccg ttc tgg ggt ccg cgt tgc gag cgg gtg gcg cgc<br>His Cys Ala Gln Pro Phe Trp Gly Pro Arg Cys Glu Arg Val Ala Arg<br>                1280                    1285                    1290 | 3951 |
| tcc tgc cgg gag ctg cag tgc ccg gtg ggc gtc cca tgc cag cag acg<br>Ser Cys Arg Glu Leu Gln Cys Pro Val Gly Val Pro Cys Gln Gln Thr<br>      1295                  1300                    1305 | 3999 |
| ccc cgc ggg ccg cgc tgc gcc tgc ccc cca ggg ttg tcg gga ccc tcc<br>Pro Arg Gly Pro Arg Cys Ala Cys Pro Pro Gly Leu Ser Gly Pro Ser<br>1310                      1315                    1320 | 4047 |
| tgc cgc agc ttc ccg ggg tcg ccg ccg ggg gcc agc aac gcc agc tgc<br>Cys Arg Ser Phe Pro Gly Ser Pro Pro Gly Ala Ser Asn Ala Ser Cys<br>      1325                  1330                    1335 | 4095 |
| gcg gcc gcc ccc tgt ctc cac ggg ggc tcc tgc cgc ccc gcg ccg ctc<br>Ala Ala Ala Pro Cys Leu His Gly Gly Ser Cys Arg Pro Ala Pro Leu<br>1340                      1345                    1350                    1355 | 4143 |
| gcg ccc ttc ttc cgc tgc gct tgc gcg cag ggc tgg acc ggg ccg cgc<br>Ala Pro Phe Phe Arg Cys Ala Cys Ala Gln Gly Trp Thr Gly Pro Arg<br>                1360                    1365                    1370 | 4191 |
| tgc gag gcg ccc gcc gcg gca ccc gag gtc tcg gag gag ccg cgg tgc<br>Cys Glu Ala Pro Ala Ala Ala Pro Glu Val Ser Glu Glu Pro Arg Cys<br>      1375                  1380                    1385 | 4239 |
| ccg cgc gcc gcc tgc cag gcc aag cgc ggg gac cag cgc tgc gac cgc<br>Pro Arg Ala Ala Cys Gln Ala Lys Arg Gly Asp Gln Arg Cys Asp Arg<br>1390                      1395                    1400 | 4287 |
| gag tgc aac agc cca ggc tgc ggc tgg gac ggc ggc gac tgc tcg ctg<br>Glu Cys Asn Ser Pro Gly Cys Gly Trp Asp Gly Gly Asp Cys Ser Leu<br>      1405                  1410                    1415 | 4335 |
| agc gtg ggc gac ccc tgg cgg caa tgc gag gcg ctg cag tgc tgg cgc<br>Ser Val Gly Asp Pro Trp Arg Gln Cys Glu Ala Leu Gln Cys Trp Arg<br>1420                      1425                    1430                    1435 | 4383 |

-continued

| | | |
|---|---|---|
| ctc ttc aac aac agc cgc tgc gac ccc gcc tgc agc tcg ccc gcc tgc<br>Leu Phe Asn Asn Ser Arg Cys Asp Pro Ala Cys Ser Ser Pro Ala Cys<br>  1440                1445                1450 | | 4431 |
| ctc tac gac aac ttc gac tgc cac gcc ggt ggc cgc gag cgc act tgc<br>Leu Tyr Asp Asn Phe Asp Cys His Ala Gly Gly Arg Glu Arg Thr Cys<br>     1455                1460                1465 | | 4479 |
| aac ccg gtg tac gag aag tac tgc gcc gac cac ttt gcc gac ggc cgc<br>Asn Pro Val Tyr Glu Lys Tyr Cys Ala Asp His Phe Ala Asp Gly Arg<br>1470                1475                1480 | | 4527 |
| tgc gac cag ggc tgc aac acg gag gag tgc ggc tgg gat ggg ctg gat<br>Cys Asp Gln Gly Cys Asn Thr Glu Glu Cys Gly Trp Asp Gly Leu Asp<br>  1485                1490                1495 | | 4575 |
| tgt gcc agc gag gtg ccg gcc ctg ctg gcc cgc ggc gtg ctg gtg ctc<br>Cys Ala Ser Glu Val Pro Ala Leu Leu Ala Arg Gly Val Leu Val Leu<br>1500                1505                1510                1515 | | 4623 |
| aca gtg ctg ctg ccg ccg gag gag cta ctg cgt tcc agc gcc gac ttt<br>Thr Val Leu Leu Pro Pro Glu Glu Leu Leu Arg Ser Ser Ala Asp Phe<br>    1520                1525                1530 | | 4671 |
| ctg cag cgg ctc agc gcc atc ctg cgc acc tcg ctg cgc ttc cgc ctg<br>Leu Gln Arg Leu Ser Ala Ile Leu Arg Thr Ser Leu Arg Phe Arg Leu<br>1535                1540                1545 | | 4719 |
| gac gcg cac ggc cag gcc atg gtc ttc cct tac cac cgg cct agt cct<br>Asp Ala His Gly Gln Ala Met Val Phe Pro Tyr His Arg Pro Ser Pro<br>  1550                1555                1560 | | 4767 |
| ggc tcc gaa ccc cgg gcc cgt cgg gag ctg gcc ccc gag gtg atc ggc<br>Gly Ser Glu Pro Arg Ala Arg Arg Glu Leu Ala Pro Glu Val Ile Gly<br>    1565                1570                1575 | | 4815 |
| tcg gta gta atg ctg gag att gac aac cgg ctc tgc ctg cag tcg cct<br>Ser Val Val Met Leu Glu Ile Asp Asn Arg Leu Cys Leu Gln Ser Pro<br>1580                1585                1590                1595 | | 4863 |
| gag aat gat cac tgc ttc ccc gat gcc cag agc gcc gct gac tac ctg<br>Glu Asn Asp His Cys Phe Pro Asp Ala Gln Ser Ala Ala Asp Tyr Leu<br>    1600                1605                1610 | | 4911 |
| gga gcg ttg tca gcg gtg gag cgc ctg gac ttc ccg tac cca ctg cgg<br>Gly Ala Leu Ser Ala Val Glu Arg Leu Asp Phe Pro Tyr Pro Leu Arg<br>  1615                1620                1625 | | 4959 |
| gac gtg cgg ggg gag ccg ctg gag cct cca gaa ccc agc gtc ccg ctg<br>Asp Val Arg Gly Glu Pro Leu Glu Pro Pro Glu Pro Ser Val Pro Leu<br>    1630                1635                1640 | | 5007 |
| ctg cca ctg cta gtg gcg ggc gct gtc ttg ctg ctg gtc att ctc gtc<br>Leu Pro Leu Leu Val Ala Gly Ala Val Leu Leu Leu Val Ile Leu Val<br>1645                1650                1655 | | 5055 |
| ctg ggt gtc atg gtg gcc cgg cgc aag cgc gag cac agc acc ctc tgg<br>Leu Gly Val Met Val Ala Arg Arg Lys Arg Glu His Ser Thr Leu Trp<br>1660                1665                1670                1675 | | 5103 |
| ttc cct gag ggc ttc tca ctg cac aag gac gtg gcc tct ggt cac aag<br>Phe Pro Glu Gly Phe Ser Leu His Lys Asp Val Ala Ser Gly His Lys<br>    1680                1685                1690 | | 5151 |
| ggc cgg cgg gaa ccc gtg ggc cag gac gcg ctg ggc atg aag aac atg<br>Gly Arg Arg Glu Pro Val Gly Gln Asp Ala Leu Gly Met Lys Asn Met<br>  1695                1700                1705 | | 5199 |
| gcc aag ggt gag agc ctg atg ggg gag gtg gcc aca gac tgg atg gac<br>Ala Lys Gly Glu Ser Leu Met Gly Glu Val Ala Thr Asp Trp Met Asp<br>    1710                1715                1720 | | 5247 |
| aca gag tgc cca gag gcc aag cgg cta aag gta gag gag cca ggc atg<br>Thr Glu Cys Pro Glu Ala Lys Arg Leu Lys Val Glu Glu Pro Gly Met<br>1725                1730                1735 | | 5295 |
| ggg gct gag gag gct gtg gat tgc cgt cag tgg act caa cac cat ctg<br>Gly Ala Glu Glu Ala Val Asp Cys Arg Gln Trp Thr Gln His His Leu<br>1740                1745                1750                1755 | | 5343 |

-continued

| | |
|---|---|
| gtt gct gct gac atc cgc gtg gca cca gcc atg gca ctg aca cca cca<br>Val Ala Ala Asp Ile Arg Val Ala Pro Ala Met Ala Leu Thr Pro Pro<br>            1760                    1765                  1770 | 5391 |
| cag ggc gac gca gat gct gat ggc atg gat gtc aat gtg cgt ggc cca<br>Gln Gly Asp Ala Asp Ala Asp Gly Met Asp Val Asn Val Arg Gly Pro<br>1775                  1780                    1785 | 5439 |
| gat ggc ttc acc ccg cta atg ctg gct tcc ttc tgt ggg ggg gct ctg<br>Asp Gly Phe Thr Pro Leu Met Leu Ala Ser Phe Cys Gly Gly Ala Leu<br>            1790                    1795                  1800 | 5487 |
| gag cca atg cca act gaa gag gat gag gca gat gac aca tca gct agc<br>Glu Pro Met Pro Thr Glu Glu Asp Glu Ala Asp Asp Thr Ser Ala Ser<br>1805                  1810                    1815 | 5535 |
| atc atc tcc gac ctg atc tgc cag ggg gct cag ctt ggg gca cgg act<br>Ile Ile Ser Asp Leu Ile Cys Gln Gly Ala Gln Leu Gly Ala Arg Thr<br>1820                  1825                    1830                  1835 | 5583 |
| gac cgt act ggc gag act gct ttg cac ctg gct gcc cgt tat gcc cgt<br>Asp Arg Thr Gly Glu Thr Ala Leu His Leu Ala Ala Arg Tyr Ala Arg<br>            1840                    1845                  1850 | 5631 |
| gct gat gca gcc aag cgg ctg ctg gat gct ggg gca gac acc aat gcc<br>Ala Asp Ala Ala Lys Arg Leu Leu Asp Ala Gly Ala Asp Thr Asn Ala<br>1855                  1860                    1865 | 5679 |
| cag gac cac tca ggc cgc act ccc ctg cac aca gct gtc aca gcc gat<br>Gln Asp His Ser Gly Arg Thr Pro Leu His Thr Ala Val Thr Ala Asp<br>            1870                    1875                  1880 | 5727 |
| gcc cag ggt gtc ttc cag att ctc atc cga aac cgc tct aca gac ttg<br>Ala Gln Gly Val Phe Gln Ile Leu Ile Arg Asn Arg Ser Thr Asp Leu<br>1885                  1890                    1895 | 5775 |
| gat gcc cgc atg gca gat ggc tca acg gca ctg atc ctg gcg gcc cgc<br>Asp Ala Arg Met Ala Asp Gly Ser Thr Ala Leu Ile Leu Ala Ala Arg<br>1900                  1905                    1910                  1915 | 5823 |
| ctg gca gta gag ggc atg gtg gaa gag ctc atc gcc agc cat gct gat<br>Leu Ala Val Glu Gly Met Val Glu Glu Leu Ile Ala Ser His Ala Asp<br>            1920                    1925                  1930 | 5871 |
| gtc aat gct gtg gat gag ctt ggg aaa tca gcc tta cac tgg gct gcg<br>Val Asn Ala Val Asp Glu Leu Gly Lys Ser Ala Leu His Trp Ala Ala<br>1935                  1940                    1945 | 5919 |
| gct gtg aac aac gtg gaa gcc act ttg gcc ctg ctc aaa aat gga gcc<br>Ala Val Asn Asn Val Glu Ala Thr Leu Ala Leu Leu Lys Asn Gly Ala<br>            1950                    1955                  1960 | 5967 |
| aat aag gac atg cag gat agc aag gag gag acc ccc cta ttc ctg gcc<br>Asn Lys Asp Met Gln Asp Ser Lys Glu Glu Thr Pro Leu Phe Leu Ala<br>1965                  1970                    1975 | 6015 |
| gcc cgc gag ggc agc tat gag gct gcc aag ctg ctg ttg gac cac ttt<br>Ala Arg Glu Gly Ser Tyr Glu Ala Ala Lys Leu Leu Leu Asp His Phe<br>1980                  1985                    1990                  1995 | 6063 |
| gcc aac cgt gag atc acc gac cac ctg gac agg ctg ccg cgg gac gta<br>Ala Asn Arg Glu Ile Thr Asp His Leu Asp Arg Leu Pro Arg Asp Val<br>            2000                    2005                  2010 | 6111 |
| gcc cag gag aga ctg cac cag gac atc gtg cgc ttg ctg gat caa ccc<br>Ala Gln Glu Arg Leu His Gln Asp Ile Val Arg Leu Leu Asp Gln Pro<br>2015                  2020                    2025 | 6159 |
| agt ggg ccc cgc agc ccc ccc ggt ccc cac ggc ctg ggg cct ctg ctc<br>Ser Gly Pro Arg Ser Pro Pro Gly Pro His Gly Leu Gly Pro Leu Leu<br>            2030                    2035                  2040 | 6207 |
| tgt cct cca ggg gcc ttc ctc cct ggc ctc aaa gcg gca cag tcg ggg<br>Cys Pro Pro Gly Ala Phe Leu Pro Gly Leu Lys Ala Ala Gln Ser Gly<br>2045                  2050                    2055 | 6255 |
| tcc aag aag agc agg agg ccc ccc ggg aag gcg ggg ctg ggg ccg cag<br>Ser Lys Lys Ser Arg Arg Pro Pro Gly Lys Ala Gly Leu Gly Pro Gln<br>2060                  2065                    2070                  2075 | 6303 |

| | |
|---|---|
| ggg ccc cgg ggg cgg ggc aag aag ctg acg ctg gcc tgc ccg ggc ccc<br>Gly Pro Arg Gly Arg Gly Lys Lys Leu Thr Leu Ala Cys Pro Gly Pro<br>                2080                           2085                       2090 | 6351 |
| ctg gct gac agc tcg gtc acg ctg tcg ccc gtg gac tcg ctg gac tcc<br>Leu Ala Asp Ser Ser Val Thr Leu Ser Pro Val Asp Ser Leu Asp Ser<br>                2095                           2100                       2105 | 6399 |
| ccg cgg cct ttc ggt ggg ccc cct gct tcc cct ggt ggc ttc ccc ctt<br>Pro Arg Pro Phe Gly Gly Pro Pro Ala Ser Pro Gly Gly Phe Pro Leu<br>                2110                           2115                       2120 | 6447 |
| gag ggg ccc tat gca gct gcc act gcc act gca gtg tct ctg gca cag<br>Glu Gly Pro Tyr Ala Ala Ala Thr Ala Thr Ala Val Ser Leu Ala Gln<br>                2125                           2130                       2135 | 6495 |
| ctt ggt ggc cca ggc cgg gca ggt cta ggg cgc cag ccc cct gga gga<br>Leu Gly Gly Pro Gly Arg Ala Gly Leu Gly Arg Gln Pro Pro Gly Gly<br>2140                       2145                       2150                       2155 | 6543 |
| tgt gta ctc agc ctg ggc ctg ctg aac cct gtg gct gtg ccc ctc gat<br>Cys Val Leu Ser Leu Gly Leu Leu Asn Pro Val Ala Val Pro Leu Asp<br>                2160                           2165                       2170 | 6591 |
| tgg gcc cgg ctg ccc cca cct gcc cct cca ggc ccc tcg ttc ctg ctg<br>Trp Ala Arg Leu Pro Pro Pro Ala Pro Pro Gly Pro Ser Phe Leu Leu<br>                2175                           2180                       2185 | 6639 |
| cca ctg gcg ccg gga ccc cag ctg ctc aac cca ggg acc ccc gtc tcc<br>Pro Leu Ala Pro Gly Pro Gln Leu Leu Asn Pro Gly Thr Pro Val Ser<br>                2190                           2195                       2200 | 6687 |
| ccg cag gag cgg ccc ccg cct tac ctg gca gtc cca gga cat ggc gag<br>Pro Gln Glu Arg Pro Pro Pro Tyr Leu Ala Val Pro Gly His Gly Glu<br>                2205                           2210                       2215 | 6735 |
| gag tac ccg gtg gct ggg gca cac agc agc ccc cca aag gcc cgc ttc<br>Glu Tyr Pro Val Ala Gly Ala His Ser Ser Pro Pro Lys Ala Arg Phe<br>2220                       2225                       2230                       2235 | 6783 |
| ctg cgg gtt ccc agt gag cac cct tac ctg acc cca tcc ccc gaa tcc<br>Leu Arg Val Pro Ser Glu His Pro Tyr Leu Thr Pro Ser Pro Glu Ser<br>                2240                           2245                       2250 | 6831 |
| cct gag cac tgg gcc agc ccc tca cct ccc tcc ctc tca gac tgg tcc<br>Pro Glu His Trp Ala Ser Pro Ser Pro Pro Ser Leu Ser Asp Trp Ser<br>                2255                           2260                       2265 | 6879 |
| gaa tcc acg cct agc cca gcc act gcc act ggg gcc atg gcc acc acc<br>Glu Ser Thr Pro Ser Pro Ala Thr Ala Thr Gly Ala Met Ala Thr Thr<br>                2270                           2275                       2280 | 6927 |
| act ggg gca ctg cct gcc cag cca ctt ccc ttg tct gtt ccc agc tcc<br>Thr Gly Ala Leu Pro Ala Gln Pro Leu Pro Leu Ser Val Pro Ser Ser<br>                2285                           2290                       2295 | 6975 |
| ctt gct cag gcc cag acc cag ctg ggg ccc cag ccg gaa gtt acc ccc<br>Leu Ala Gln Ala Gln Thr Gln Leu Gly Pro Gln Pro Glu Val Thr Pro<br>2300                       2305                       2310                       2315 | 7023 |
| aag agg caa gtg ttg gcc tgagacgctc gtcagttctt agatcttggg<br>Lys Arg Gln Val Leu Ala<br>                2320 | 7071 |
| ggcctaaaga gaccccgtc ctgcctcctt tctttctctg tctcttcctt cctttagtc | 7131 |
| tttttcatcc tcttctcttt ccaccaaccc tcctgcatcc ttgccttgca gcgtgaccga | 7191 |
| gataggtcat cagcccaggg cttcagtctt cctttattta taatgggtgg gggctaccac | 7251 |
| ccacccctctc agtcttgtga agagtctggg acctccttct tccccacttc tctcttccct | 7311 |
| cattcctttc tctctcctcc tggcctctca tttccttaca ctctgacatg aatgaattat | 7371 |
| tattattttt cttttctttt tttttttttac attttgtata gaaacaaatt catttaaaca | 7431 |
| aacttattat tattatttttt tacaaaatat atatatggag atgctccctc cccctgtgaa | 7491 |
| cccccccagtg cccccgtggg gctgagtctg tgggcccatt cggccaagct ggattctgtg | 7551 |

-continued

```
tacctagtac acaggcatga ctgggatccc gtgtaccgag tacacgaccc aggtatgtac    7611
caagtaggca cccttgggcg cacccactgg ggccaggggt cgggggagtg ttgggagcct    7671
cctccccacc ccacctccct cacttcactg cattccagat tggacatgtt ccatagcctt    7731
gctggggaag ggcccactgc caactccctc tgccccagcc ccaccttgg ccatctccct     7791 ttgggaacta gggggctgct ggtgggaaat gggagccagg gcagatgtat gcattccttt    7851
atgtccctgt aaatgtggga ctacaagaag aggagctgcc tgagtggtac tttctcttcc    7911
tggtaatcct ctggcccagc cttatggcag aatagaggta ttttaggct attttgtaa      7971 tatggcttct ggtcaaaatc cctgtgtagc tgaattccca agccctgcat tgtacagccc    8031
cccactcccc tcaccaccta ataaggaat agttaacact caaaaaaaaa aaaaaaaaa      8091
```

<210> SEQ ID NO 2
<211> LENGTH: 2321
<212> TYPE: PRT
<213> ORGANISM: Homo sapiens
<220> FEATURE:
<223> OTHER INFORMATION: human ADNc Notch 3

<400> SEQUENCE: 2

```
Met Gly Pro Gly Ala Arg Gly Arg Arg Arg Arg Pro Met Ser
  1               5                  10                  15

Pro Pro Pro Pro Pro Pro Val Arg Ala Leu Pro Leu Leu Leu
                 20                  25                  30

Leu Ala Gly Pro Gly Ala Ala Ala Pro Pro Cys Leu Asp Gly Ser Pro
                 35                  40                  45

Cys Ala Asn Gly Gly Arg Cys Thr Gln Leu Pro Ser Arg Glu Ala Ala
         50                  55                  60

Cys Leu Cys Pro Pro Gly Trp Val Gly Glu Arg Cys Gln Leu Glu Asp
 65                  70                  75                  80

Pro Cys His Ser Gly Pro Cys Ala Gly Arg Gly Val Cys Gln Ser Ser
                 85                  90                  95

Val Val Ala Gly Thr Ala Arg Phe Ser Cys Arg Cys Pro Arg Gly Phe
                100                 105                 110

Arg Gly Pro Asp Cys Ser Leu Pro Asp Pro Cys Leu Ser Ser Pro Cys
            115                 120                 125

Ala His Gly Ala Arg Cys Ser Val Gly Pro Asp Gly Arg Phe Leu Cys
        130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270
```

-continued

```
Glu Asp Val Asp Glu Cys Gln Leu Gln Pro Asn Ala Cys His Asn Gly
            275                 280                 285
Gly Thr Cys Phe Asn Thr Leu Gly Gly His Ser Cys Val Cys Val Asn
        290                 295                 300
Gly Trp Thr Gly Glu Ser Cys Ser Gln Asn Ile Asp Asp Cys Ala Thr
305                 310                 315                 320
Ala Val Cys Phe His Gly Ala Thr Cys His Asp Arg Val Ala Ser Phe
                325                 330                 335
Tyr Cys Ala Cys Pro Met Gly Lys Thr Gly Leu Leu Cys His Leu Asp
            340                 345                 350
Asp Ala Cys Val Ser Asn Pro Cys His Glu Asp Ala Ile Cys Asp Thr
        355                 360                 365
Asn Pro Val Asn Gly Arg Ala Ile Cys Thr Cys Pro Pro Gly Phe Thr
370                 375                 380
Gly Gly Ala Cys Asp Gln Asp Val Asp Glu Cys Ser Ile Gly Ala Asn
385                 390                 395                 400
Pro Cys Glu His Leu Gly Arg Cys Val Asn Thr Gln Gly Ser Phe Leu
                405                 410                 415
Cys Gln Cys Gly Arg Gly Tyr Thr Gly Pro Arg Cys Glu Thr Asp Val
            420                 425                 430
Asn Glu Cys Leu Ser Gly Pro Cys Arg Asn Gln Ala Thr Cys Leu Asp
        435                 440                 445
Arg Ile Gly Gln Phe Thr Cys Ile Cys Met Ala Gly Phe Thr Gly Thr
450                 455                 460
Tyr Cys Glu Val Asp Ile Asp Glu Cys Gln Ser Ser Pro Cys Val Asn
465                 470                 475                 480
Gly Gly Val Cys Lys Asp Arg Val Asn Gly Phe Ser Cys Thr Cys Pro
                485                 490                 495
Ser Gly Phe Ser Gly Ser Thr Cys Gln Leu Asp Val Asp Glu Cys Ala
            500                 505                 510
Ser Thr Pro Cys Arg Asn Gly Ala Lys Cys Val Asp Gln Pro Asp Gly
        515                 520                 525
Tyr Glu Cys Arg Cys Ala Glu Gly Phe Glu Gly Thr Leu Cys Asp Arg
        530                 535                 540
Asn Val Asp Asp Cys Ser Pro Asp Pro Cys His His Gly Arg Cys Val
545                 550                 555                 560
Asp Gly Ile Ala Ser Phe Ser Cys Ala Cys Ala Pro Gly Tyr Thr Gly
                565                 570                 575
Thr Arg Cys Glu Ser Gln Val Asp Glu Cys Arg Ser Gln Pro Cys Arg
            580                 585                 590
His Gly Gly Lys Cys Leu Asp Leu Val Asp Lys Tyr Leu Cys Arg Cys
        595                 600                 605
Pro Ser Gly Thr Thr Gly Val Asn Cys Glu Val Asn Ile Asp Asp Cys
        610                 615                 620
Ala Ser Asn Pro Cys Thr Phe Gly Val Cys Arg Asp Gly Ile Asn Arg
625                 630                 635                 640
Tyr Asp Cys Val Cys Gln Pro Gly Phe Thr Gly Pro Leu Cys Asn Val
                645                 650                 655
Glu Ile Asn Glu Cys Ala Ser Ser Pro Cys Gly Glu Gly Gly Ser Cys
            660                 665                 670
Val Asp Gly Glu Asn Gly Phe Arg Cys Leu Cys Pro Pro Gly Ser Leu
        675                 680                 685
```

-continued

```
Pro Pro Leu Cys Leu Pro Pro Ser His Pro Cys Ala His Glu Pro Cys
    690             695             700
Ser His Gly Ile Cys Tyr Asp Ala Pro Gly Gly Phe Arg Cys Val Cys
705             710             715             720
Glu Pro Gly Trp Ser Gly Pro Arg Cys Ser Gln Ser Leu Ala Arg Asp
            725             730             735
Ala Cys Glu Ser Gln Pro Cys Arg Ala Gly Gly Thr Cys Ser Ser Asp
            740             745             750
Gly Met Gly Phe His Cys Thr Cys Pro Pro Gly Val Gln Gly Arg Gln
        755             760             765
Cys Glu Leu Leu Ser Pro Cys Thr Pro Asn Pro Cys Glu His Gly Gly
    770             775             780
Arg Cys Glu Ser Ala Pro Gly Gln Leu Pro Val Cys Ser Cys Pro Gln
785             790             795             800
Gly Trp Gln Gly Pro Arg Cys Gln Gln Asp Val Asp Glu Cys Ala Gly
            805             810             815
Pro Ala Pro Cys Gly Pro His Gly Ile Cys Thr Asn Leu Ala Gly Ser
            820             825             830
Phe Ser Cys Thr Cys His Gly Gly Tyr Thr Gly Pro Ser Cys Asp Gln
        835             840             845
Asp Ile Asn Asp Cys Asp Pro Asn Pro Cys Leu Asn Gly Gly Ser Cys
    850             855             860
Gln Asp Gly Val Gly Ser Phe Ser Cys Ser Cys Leu Pro Gly Phe Ala
865             870             875             880
Gly Pro Arg Cys Ala Arg Asp Val Asp Glu Cys Leu Ser Asn Pro Cys
            885             890             895
Gly Pro Gly Thr Cys Thr Asp His Val Ala Ser Phe Thr Cys Thr Cys
            900             905             910
Pro Pro Gly Tyr Gly Gly Phe His Cys Glu Gln Asp Leu Pro Asp Cys
        915             920             925
Ser Pro Ser Ser Cys Phe Asn Gly Gly Thr Cys Val Asp Gly Val Asn
    930             935             940
Ser Phe Ser Cys Leu Cys Arg Pro Gly Tyr Thr Gly Ala His Cys Gln
945             950             955             960
His Glu Ala Asp Pro Cys Leu Ser Arg Pro Cys Leu His Gly Gly Val
            965             970             975
Cys Ser Ala Ala His Pro Gly Phe Arg Cys Thr Cys Leu Glu Ser Phe
            980             985             990
Thr Gly Pro Gln Cys Gln Thr Leu Val Asp Trp Cys Ser Arg Gln Pro
        995             1000            1005
Cys Gln Asn Gly Gly Arg Cys Val Gln Thr Gly Ala Tyr Cys Leu Cys
    1010            1015            1020
Pro Pro Gly Trp Ser Gly Arg Leu Cys Asp Ile Arg Ser Leu Pro Cys
1025            1030            1035            1040
Arg Glu Ala Ala Ala Gln Ile Gly Val Arg Leu Glu Gln Leu Cys Gln
            1045            1050            1055
Ala Gly Gly Gln Cys Val Asp Glu Asp Ser Ser His Tyr Cys Val Cys
            1060            1065            1070
Pro Glu Gly Arg Thr Gly Ser His Cys Glu Gln Glu Val Asp Pro Cys
        1075            1080            1085
Leu Ala Gln Pro Cys Gln His Gly Gly Thr Cys Arg Gly Tyr Met Gly
    1090            1095            1100
```

-continued

```
Gly Tyr Met Cys Glu Cys Leu Pro Gly Tyr Asn Gly Asp Asn Cys Glu
1105                1110                1115                1120

Asp Asp Val Asp Glu Cys Ala Ser Gln Pro Cys Gln His Gly Gly Ser
            1125                1130                1135

Cys Ile Asp Leu Val Ala Arg Tyr Leu Cys Ser Cys Pro Pro Gly Thr
        1140                1145                1150

Leu Gly Val Leu Cys Glu Ile Asn Glu Asp Asp Cys Gly Pro Gly Pro
        1155                1160                1165

Pro Leu Asp Ser Gly Pro Arg Cys Leu His Asn Gly Thr Cys Val Asp
    1170                1175                1180

Leu Val Gly Gly Phe Arg Cys Thr Cys Pro Pro Gly Tyr Thr Gly Leu
1185                1190                1195                1200

Arg Cys Glu Ala Asp Ile Asn Glu Cys Arg Ser Gly Ala Cys His Ala
                1205                1210                1215

Ala His Thr Arg Asp Cys Leu Gln Asp Pro Gly Gly Gly Phe Arg Cys
            1220                1225                1230

Leu Cys His Ala Gly Phe Ser Gly Pro Arg Cys Gln Thr Val Leu Ser
        1235                1240                1245

Pro Cys Glu Ser Gln Pro Cys Gln His Gly Gly Gln Cys Arg Pro Ser
    1250                1255                1260

Pro Gly Pro Gly Gly Gly Leu Thr Phe Thr Cys His Cys Ala Gln Pro
1265                1270                1275                1280

Phe Trp Gly Pro Arg Cys Glu Arg Val Ala Arg Ser Cys Arg Glu Leu
                1285                1290                1295

Gln Cys Pro Val Gly Val Pro Cys Gln Gln Thr Pro Arg Gly Pro Arg
            1300                1305                1310

Cys Ala Cys Pro Pro Gly Leu Ser Gly Pro Ser Cys Arg Ser Phe Pro
        1315                1320                1325

Gly Ser Pro Pro Gly Ala Ser Asn Ala Ser Cys Ala Ala Ala Pro Cys
    1330                1335                1340

Leu His Gly Gly Ser Cys Arg Pro Ala Pro Leu Ala Pro Phe Phe Arg
1345                1350                1355                1360

Cys Ala Cys Ala Gln Gly Trp Thr Gly Pro Arg Cys Glu Ala Pro Ala
            1365                1370                1375

Ala Ala Pro Glu Val Ser Glu Glu Pro Arg Cys Pro Arg Ala Ala Cys
            1380                1385                1390

Gln Ala Lys Arg Gly Asp Gln Arg Cys Asp Arg Glu Cys Asn Ser Pro
        1395                1400                1405

Gly Cys Gly Trp Asp Gly Gly Asp Cys Ser Leu Ser Val Gly Asp Pro
    1410                1415                1420

Trp Arg Gln Cys Glu Ala Leu Gln Cys Trp Arg Leu Phe Asn Asn Ser
1425                1430                1435                1440

Arg Cys Asp Pro Ala Cys Ser Ser Pro Ala Cys Leu Tyr Asp Asn Phe
            1445                1450                1455

Asp Cys His Ala Gly Gly Arg Glu Arg Thr Cys Asn Pro Val Tyr Glu
            1460                1465                1470

Lys Tyr Cys Ala Asp His Phe Ala Asp Gly Arg Cys Asp Gln Gly Cys
        1475                1480                1485

Asn Thr Glu Glu Cys Gly Trp Asp Gly Leu Asp Cys Ala Ser Glu Val
    1490                1495                1500

Pro Ala Leu Leu Ala Arg Gly Val Leu Val Leu Thr Val Leu Leu Pro
1505                1510                1515                1520
```

-continued

```
Pro Glu Glu Leu Leu Arg Ser Ser Ala Asp Phe Leu Gln Arg Leu Ser
            1525                1530                1535

Ala Ile Leu Arg Thr Ser Leu Arg Phe Arg Leu Asp Ala His Gly Gln
        1540                1545                1550

Ala Met Val Phe Pro Tyr His Arg Pro Ser Pro Gly Ser Glu Pro Arg
    1555                1560                1565

Ala Arg Arg Glu Leu Ala Pro Glu Val Ile Gly Ser Val Val Met Leu
1570                1575                1580

Glu Ile Asp Asn Arg Leu Cys Leu Gln Ser Pro Glu Asn Asp His Cys
1585                1590                1595                1600

Phe Pro Asp Ala Gln Ser Ala Ala Asp Tyr Leu Gly Ala Leu Ser Ala
            1605                1610                1615

Val Glu Arg Leu Asp Phe Pro Tyr Pro Leu Arg Asp Val Arg Gly Glu
        1620                1625                1630

Pro Leu Glu Pro Pro Glu Pro Ser Val Pro Leu Leu Pro Leu Leu Val
    1635                1640                1645

Ala Gly Ala Val Leu Leu Leu Val Ile Leu Val Leu Gly Val Met Val
1650                1655                1660

Ala Arg Arg Lys Arg Glu His Ser Thr Leu Trp Phe Pro Glu Gly Phe
1665                1670                1675                1680

Ser Leu His Lys Asp Val Ala Ser Gly His Lys Gly Arg Arg Glu Pro
            1685                1690                1695

Val Gly Gln Asp Ala Leu Gly Met Lys Asn Met Ala Lys Gly Glu Ser
        1700                1705                1710

Leu Met Gly Glu Val Ala Thr Asp Trp Met Asp Thr Glu Cys Pro Glu
    1715                1720                1725

Ala Lys Arg Leu Lys Val Glu Glu Pro Gly Met Gly Ala Glu Glu Ala
1730                1735                1740

Val Asp Cys Arg Gln Trp Thr Gln His His Leu Val Ala Ala Asp Ile
1745                1750                1755                1760

Arg Val Ala Pro Ala Met Ala Leu Thr Pro Pro Gln Gly Asp Ala Asp
            1765                1770                1775

Ala Asp Gly Met Asp Val Asn Val Arg Gly Pro Asp Gly Phe Thr Pro
        1780                1785                1790

Leu Met Leu Ala Ser Phe Cys Gly Gly Ala Leu Glu Pro Met Pro Thr
    1795                1800                1805

Glu Glu Asp Glu Ala Asp Asp Thr Ser Ala Ser Ile Ile Ser Asp Leu
1810                1815                1820

Ile Cys Gln Gly Ala Gln Leu Gly Ala Arg Thr Asp Arg Thr Gly Glu
1825                1830                1835                1840

Thr Ala Leu His Leu Ala Ala Arg Tyr Ala Arg Ala Asp Ala Ala Lys
            1845                1850                1855

Arg Leu Leu Asp Ala Gly Ala Asp Thr Asn Ala Gln Asp His Ser Gly
        1860                1865                1870

Arg Thr Pro Leu His Thr Ala Val Thr Ala Asp Ala Gln Gly Val Phe
    1875                1880                1885

Gln Ile Leu Ile Arg Asn Arg Ser Thr Asp Leu Asp Ala Arg Met Ala
1890                1895                1900

Asp Gly Ser Thr Ala Leu Ile Leu Ala Ala Arg Leu Ala Val Glu Gly
1905                1910                1915                1920

Met Val Glu Glu Leu Ile Ala Ser His Ala Asp Val Asn Ala Val Asp
            1925                1930                1935
```

-continued

```
Glu Leu Gly Lys Ser Ala Leu His Trp Ala Ala Ala Val Asn Asn Val
        1940                1945                1950

Glu Ala Thr Leu Ala Leu Leu Lys Asn Gly Ala Asn Lys Asp Met Gln
        1955                1960                1965

Asp Ser Lys Glu Glu Thr Pro Leu Phe Leu Ala Ala Arg Glu Gly Ser
    1970                1975                1980

Tyr Glu Ala Ala Lys Leu Leu Leu Asp His Phe Ala Asn Arg Glu Ile
1985                1990                1995                2000

Thr Asp His Leu Asp Arg Leu Pro Arg Asp Val Ala Gln Glu Arg Leu
            2005                2010                2015

His Gln Asp Ile Val Arg Leu Leu Asp Gln Pro Ser Gly Pro Arg Ser
            2020                2025                2030

Pro Pro Gly Pro His Gly Leu Gly Pro Leu Leu Cys Pro Pro Gly Ala
        2035                2040                2045

Phe Leu Pro Gly Leu Lys Ala Ala Gln Ser Gly Ser Lys Lys Ser Arg
        2050                2055                2060

Arg Pro Pro Gly Lys Ala Gly Leu Gly Pro Gln Gly Pro Arg Gly Arg
2065                2070                2075                2080

Gly Lys Lys Leu Thr Leu Ala Cys Pro Gly Pro Leu Ala Asp Ser Ser
            2085                2090                2095

Val Thr Leu Ser Pro Val Asp Ser Leu Asp Ser Pro Arg Pro Phe Gly
        2100                2105                2110

Gly Pro Pro Ala Ser Pro Gly Gly Phe Pro Leu Glu Gly Pro Tyr Ala
        2115                2120                2125

Ala Ala Thr Ala Thr Ala Val Ser Leu Ala Gln Leu Gly Gly Pro Gly
    2130                2135                2140

Arg Ala Gly Leu Gly Arg Gln Pro Pro Gly Gly Cys Val Leu Ser Leu
2145                2150                2155                2160

Gly Leu Leu Asn Pro Val Ala Val Pro Leu Asp Trp Ala Arg Leu Pro
            2165                2170                2175

Pro Pro Ala Pro Pro Gly Pro Ser Phe Leu Leu Pro Leu Ala Pro Gly
        2180                2185                2190

Pro Gln Leu Leu Asn Pro Gly Thr Pro Val Ser Pro Gln Glu Arg Pro
        2195                2200                2205

Pro Pro Tyr Leu Ala Val Pro Gly His Gly Glu Glu Tyr Pro Val Ala
        2210                2215                2220

Gly Ala His Ser Ser Pro Pro Lys Ala Arg Phe Leu Arg Val Pro Ser
2225                2230                2235                2240

Glu His Pro Tyr Leu Thr Pro Ser Pro Glu Ser Pro Glu His Trp Ala
            2245                2250                2255

Ser Pro Ser Pro Pro Ser Leu Ser Asp Trp Ser Glu Ser Thr Pro Ser
        2260                2265                2270

Pro Ala Thr Ala Thr Gly Ala Met Ala Thr Thr Thr Gly Ala Leu Pro
        2275                2280                2285

Ala Gln Pro Leu Pro Leu Ser Val Pro Ser Ser Leu Ala Gln Ala Gln
    2290                2295                2300

Thr Gln Leu Gly Pro Gln Pro Glu Val Thr Pro Lys Arg Gln Val Leu
2305                2310                2315                2320

Ala

<210> SEQ ID NO 3
<211> LENGTH: 15
<212> TYPE: DNA
<213> ORGANISM: Artificial Sequence
```

```
<220> FEATURE:
<223> OTHER INFORMATION: Description of Artificial Sequence: primer

<400> SEQUENCE: 3
ctgcaggtga ggggc                                                    15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 4
cccacacagc ccccc                                                    15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 5
ctgcctgtga gtgcc                                                    15

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 6
gcccacaggt gccc                                                     14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 7
tccgaggtga gagg                                                     14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 8
ccctccaggc cctg                                                     14

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 9
ttcctggtga gtga                                                     14
```

-continued

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 10
cttgttaggg tttg                                                        14

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 11
ggacaggtgg gcac                                                        14

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 12
tgccacaggc cagt                                                        14

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 13
agactggtga gtgg                                                        14

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 14
cttcccaggc ctcc                                                        14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 15
ctatcggtga gggg                                                        14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: primer

```
<400> SEQUENCE: 16
tccggcaggc gcca                                              14

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 17
tggcaggtgg gtgg                                              14

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 18
tgccccaggc ttca                                              14

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 19
cctcgggtga ggac                                              14

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 20 cacccccaggc ttca                                             14

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 21
ccgagggtga ggcg                                              14

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 22
ccccacaggc tttg                                              14
```

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 23
ccacaggtgg gacc                                                        14

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 24 gccctaggt gtga                                                         14

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 25
tcacaggtgg gcaa                                                        14

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 26
ctccccaggg cccc                                                        14

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 27
tggcgggtga gggc                                                        14

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 28
cctgccaggt tccg                                                        14

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: primer

```
<400> SEQUENCE: 29
tccagggtgt gtac                                                14

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 30
cccaacagga cgtc                                                14

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 31
ggcaaggtat gccac                                               15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 32
tacccccagg cccac                                               15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 33
accccagtga gtgca                                               15

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 34
gtccgcagac ccat                                                14

<210> SEQ ID NO 35
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 35
ccccaggtgg gcgg                                                14
```

```
<210> SEQ ID NO 36
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 36
cgctccagct cctg                                                    14

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 37
tgccaggtgg gtgg                                                    14

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 38
ccctccagac gctg                                                    14

<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 39
agatcggtga gtgg                                                    14

<210> SEQ ID NO 40
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 40
ctttgcaggg gtgc                                                    14

<210> SEQ ID NO 41
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 41
tgtgaggtaa gggg                                                    14

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: primer
```

```
<400> SEQUENCE: 42
cactgaagtg tctt                                                      14

<210> SEQ ID NO 43
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 43
cgctgggtat gcca                                                      14

<210> SEQ ID NO 44
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 44
tcccccaggg gtgc                                                      14

<210> SEQ ID NO 45
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 45
tctcaggtta acct                                                      14

<210> SEQ ID NO 46
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 46
tcgctcaggt cctc                                                      14

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 47
gcccaggtag gtgtg                                                     15

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 48
gacccccagc cgttc                                                     15
```

```
<210> SEQ ID NO 49
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 49
ttgcaagtga gccc                                                      14

<210> SEQ ID NO 50
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 50
cccaccagcc cggt                                                      14

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 51
gatcgggtga gtgac                                                     15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 52
tccctgcagc tcggt                                                     15

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 53
tgcggggtgc ggcc                                                      14

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 54
tgctcttagg ggagc                                                     15

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: primer
```

```
<400> SEQUENCE: 55
catgaagtga gaac                                              14

<210> SEQ ID NO 56
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 56
tccgccagga acat                                              14

<210> SEQ ID NO 57
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 57
ctaaaggtac tgcc                                              14

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 58
cccctccagg tagag                                             15

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 59
gcccaggtca gtgac                                             15

<210> SEQ ID NO 60
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 60
ccctgcagat ggct                                              14

<210> SEQ ID NO 61
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 61
ttccaggtga gata                                              14
```

```
<210> SEQ ID NO 62
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 62
tgtcctagat tctc                                                     14

<210> SEQ ID NO 63
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 63
agcttggtag gttg                                                     14

<210> SEQ ID NO 64
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 64
ccctccaggg aaat                                                     14

<210> SEQ ID NO 65
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 65
agcaaggtga gccc                                                     14

<210> SEQ ID NO 66
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 66 cccccccagga ggag                                                    14

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 67
aaggagggag gagggag                                                  18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: primer
```

```
<400> SEQUENCE: 68
tgggggttct tgcactcc                                                 18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 69
ggttcctgcc tcccatga                                                 18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 70
tcctccacct tccttcac                                                 18

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 71
acacacaggg cccactggt                                                19

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 72
tgtgctgccc aaccaagcca                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 73
actgaccaca cccccgacta                                               20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 74
tagtcggggg tgtggtcagt                                               20
```

```
<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 75
tcatccacgt cgcttcggca                                               20

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 76
atggacgctt cctctgctc                                                19

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 77
acatagtggc cctgtgtagc                                               20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 78
atggacgctt cctctgctcc                                               20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 79
cctctgactc tcctgagtag                                               20

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 80
tgaccatcct tgcccccctt                                               19

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: primer
```

```
<400> SEQUENCE: 81
ctggcctgtg gcacacagat                                              20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 82
tggactgctg catctgtgtg                                              20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 83
acacgcctgt ggcacagtca                                              20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 84
gagctgcagt cagaatatcg                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 85
atccatggct ccctgcagag                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 86
cagagcagga agatctgcct                                              20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 87
cattcacaga cgacggagct                                              20
```

```
<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 88
atcgcactcc atccggca                                                 18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 89
acccacctgc catacaga                                                 18

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 90
cgttcacacc atagggtagc                                               20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 91
ccccttccca gacatgtctt                                               20

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 92
cttgtcggac tgtcattgg                                                19

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 93
gtgtactgct ctcaccctt                                                19

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: primer
```

<400> SEQUENCE: 94
attggtccga ggcctcactt                                              20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 95
acctggctct cgcagcgtgt                                              20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 96
ccattcccaa cccctctgtg                                              20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 97
tgcctgtgct cctggctaca                                              20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 98
tggccactcc atgccatgtt                                              20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 99
tctcatggca gccacttgcc                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 100
atgagtgtgc ttccagccca                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 101
gcagtgtctg aggctgagaa                                              20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 102
tccctggcct gactaccttc                                              20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 103
ctgcagaggg aaggtgaggt                                              20

<210> SEQ ID NO 104
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 104
aaggctatcc tgcttcc                                                 17

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 105
gaggaggagg gaagagaa                                                18

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 106
aggatgtgga cgagtgtgct                                              20

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: primer

```
<400> SEQUENCE: 107
gcttaatgac tgtgttcc                                              18

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 108
tcagactggg ctaatggggg                                            20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 109
tcgcagtgga agcctccgta                                            20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 110
gatgtggatg agtgcctgag                                            20

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 111
gtcctgctct tcaagcaga                                             19

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 112
gatcctccct cccactcctt                                            20

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 113
aggtccccag taactcca                                              18
```

```
<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 114
actgactcta agtgcttccc                                           20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 115
agcaggaggt acgtgcatga                                           20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 116
tgttcctgtg ccactctcct                                           20

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 117
acctcctctt ccctctcct                                            19

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 118
tctgtgtccc actaagctga                                           20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 119
caagaggaaa tgaagacagc                                           20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: primer
```

```
<400> SEQUENCE: 120
ttcctcttga ccacccctcg                                               20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 121
tggcaggcac ctgagcgaca                                               20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 122
caggatacac tggtttgcgc                                               20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 123
tgccacgtta tggatcagcc                                               20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 124
gatctacatg ctcccgctcg                                               20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 125
tactcctcct ccataggccg                                               20

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 126
cgttctgggg tccgcgtt                                                 18
```

```
<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 127
aagcgcagcg gaagaagggc                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 128
gcccttcttc cgctgcgctt                                              20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 129
actgcagcgc ctcgcattgc                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 130
ctgcgaccgc gagtgcaaca                                              20

<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 131
atagacagac ggatcgat                                                18

<210> SEQ ID NO 132
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 132
ctctctgcct caccctt                                                 17

<210> SEQ ID NO 133
<211> LENGTH: 17
<212> TYPE: DNA
<213> ORGANISM: Artificial Sequence
<220> FEATURE:
<223> OTHER INFORMATION: Description of Artificial Sequence: primer
```

```
<400> SEQUENCE: 133
gctggaacgc agtagct                                               17

<210> SEQ ID NO 134
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 134
tgctcacagt gctgctg                                               17

<210> SEQ ID NO 135
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 135
cacggctttt ccaggtg                                               17

<210> SEQ ID NO 136
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 136
tttgagccct ctggtcc                                               17

<210> SEQ ID NO 137
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 137
aagagcagga agcagag                                               17

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 138
tccctctgct tcctgctctt                                            20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 139
tcacaaggtc cccgtagtca                                            20
```

```
<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 140
ctcacatccc ctcttcccat                                                    20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 141
atcacgccca tcatccactg                                                    20

<210> SEQ ID NO 142
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 142
cagcaccaaa gggtg                                                         15

<210> SEQ ID NO 143
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 143 catcccttg ggagg                                                          15

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 144
atggcttcac cccgctaatg                                                    20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 145
agccaggtgc aaagcagtct                                                    20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: primer
```

<400> SEQUENCE: 146
tcagcttggg gcacggactg                                              20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 147
gcatcggctg tgacagctgt                                              20

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 148
tgttcctgcc atgacccct                                               19

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 149
caggtgacac taacccagtc                                              20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 150
tcctgacctc tctcccttc                                               20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 151
aatggcgctg tgccactgct                                              20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 152
gctactgtta gctggggttt                                              20

```
<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 153
tgatccagca agcgcacgat                                              20

<210> SEQ ID NO 154
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 154
tcaccgacca cctggaca                                                18

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 155
accaagctgt gccagaga                                                18

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 156
tccaagaaga gcaggagg                                                18

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 157
accaagctgt gccagaga                                                18

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 158
cagtgtctct ggcacagctt                                              20

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: primer
```

```
<400> SEQUENCE: 159
tcctgggact gccaggtaa                                          19

<210> SEQ ID NO 160
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 160
agctgctcaa cccaggga                                           18

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 161
gtggattcgg accagtct                                           18

<210> SEQ ID NO 162
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 162
gaatcccctg agcact                                             16

<210> SEQ ID NO 163
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 163
ctaagaactg acgagc                                             16
```

GENE INVOLVED IN CADASIL, METHOD OF DIAGNOSIS AND THERAPEUTIC APPLICATION

This application is a division of application Ser. No. 09/230,652, filed Jul. 31, 1997, as PCT/FR97/01433, and which entered the U.S. National Stage on Jan. 29, 1999. U.S. application Ser. No. 09/230,652 is hereby incorporated in its entirety herein by reference.

The present invention relates to the demonstration of the involvement of the Notch3 protein in CADASIL thus allowing in particular a diagnosis of a predisposition to certain neurological disorders, in particular CADASIL, and models which make it possible to test the therapies possible for this type of pathology.

CADASIL or "Cerebral Autosomal Dominant Arteriopathy with Subcortical Infarcts and Leukoencephalopathy" has recently been identified as a cause of cerebral attacks and of dementia whose main characteristics include recidivous subcortical infarcts, migraines and a vascular dementia, in association with MRI images objectivizing diffuse abnormalities of the cerebral white substance.

An anatomicopathological examination shows multiple small deep cerebral infarcts, a leukoencephalopathy and a nonatherosclerotic and nonamyloid angiopathy involving essentially the small cerebral arteries.

As its name indicates, CADASIL is a hereditary disease with a dominant autosomal character. For more information, there may be found in particular a study of the clinical spectrum of CADASIL in H. Chabriat et al., The Lancet, Vol. 346, 7 Oct. 1995.

This highly incapacitating and very often lethal disease has probably remained so far largely undiagnosed as such; the study of about one hundred families since 1993 shows that erroneous diagnoses were most often given to the patient (multiple sclerosis, Alzheimer's disease and the like). Current studies would tend to demonstrate that it is a condition which is much more widespread than what was thought during its discovery.

The research studies currently pursued have the objective of identifying diagnostic tools for the disease and, by virtue, in particular of the models and the possibilities offered by genetic engineering, of developing a possible substitute therapy.

The gene involved in CADASIL has been localized on chromosome 19 and a finer localization is in particular mentioned in two patent applications with the same inventors.

It has now been possible to identify the gene involved in CADASIL which is the Notch3 gene.

The demonstration of the involvement of Notch3 in CADASIL has been possible given the previous limits which had been mentioned especially in the patent applications in question, the first interval (size 14 cM) was D19S221–D19S215 (first patent application), and then the second interval (size 2 cM) was D19S226–D19S199 (second patent application). The region of interest was cloned into a BAC and YAC contig (continuous nucleotide sequence) and its size was estimated at 800 kb. Analysis of this region with the aid of restriction enzymes showed a very high density of NotI, EagI and SacII sites which suggested the presence of numerous genes. Among the numerous transcripts identified by cDNA selection, one transcript showed a very strong homology with a sequence situated at the coding 5' end of the mouse gene Notch3. Since other analytical factors seemed to corroborate this presence of the Notch3 gene in this situation, the latter was considered to be a good candidate gene by its position in the interval of interest.

The comparative studies carried out on known CADASIL families in comparison with healthy subjects have made it possible to identify mutations on this Notch3 gene in a large number of CADASIL subjects whereas such mutations were not observed on the healthy subjects analyzed. Since, finally, it has been possible to demonstrate the cosegregation of these mutations with the disease phenotype within effected families, the involvement of the Notch3 gene in CADASIL became incontestable.

All the point mutations observed lead to the creation or to the disappearance of a cysteine in one of the EGF domains of this protein. These mutations are clustered for a large part of them into the first six, EGFs. The clustering of the mutations is certainly important in diagnostic terms especially for the "sequential" search for these mutations.

Moreover, all these mutations lead to the presence of an odd number of cysteines in one of the EGFs (either seven, or five cysteines) instead of the six cysteines normally present. These mutations could thus result in the formation of either intra- or intermolecular (and in this case in the formation of homo- or heterodimers) aberrant disulfide bridges.

The role of a normal or abnormal dimerization in the functioning of receptors, in particular their activation, is well known.

The Notch genes have been known for a very long time, especially in drosophila and their equivalent is known in vertebrates, in particular in mice. Its English name "notch" comes from the fact that some mutations of this gene produce a notch in the wings of flies. The article by Spyros Artavanis-Tskanas et al., Science 268, 225 (1995) as well as the references which it contains indicate that the Notch proteins are essentially involved, especially in *drosophila*, in the specification of the cellular destiny during development, and although the protein is always expressed in, adult organisms, its functions in the latter remain unknown. More precisely, it appears that the product of the Notch3 gene, hereinafter "Notch3 protein", is a cell receptor which controls a cascade of cellular events and whose mutation necessarily leads to greater or lesser disruptions in this cascade which may lead to many other neurological, especially cerebrovascular, disorders.

It should be recalled that, while in the text which follows there is interest more particularly in neurological disorders, in particular cerebrovascular-type disorders and most particularly CADASIL, it is probable, given the function of the cell receptor for the product of the Notch3 gene, that impairment of this receptor can lead to a disorganization of its interaction with various ligands but also with the various partners involved in the transduction cascade. Account should be taken, in addition, of the fact that the Notch3 protein might have other functions which have not yet been demonstrated. Under these conditions, it is highly probable that conditions exhibiting similarities with CADASIL may also be involved in the case of a mutation in the Notch3 gene.

Among the relevant diseases, there may be mentioned the sporadic forms of CADASIL, that is to say which occur without a family history but following a neomutation. Notch3 might moreover be involved in other conditions which may be classified into different groups:

Migraine and Hemiplegic Migraine

It was shown that at least one of the genes involved in familial hemiplegic migraine (FHM), the dominant autosomal form of migraine with aura, was located in the same region of chromosome 19 as the CADASIL gene. It should be noted that more than 30% of patients suffering from CADASIL, a condition characterized by the repeated onset of cerebrovascular accidents and of a vascular dementia, suffered from migraine with aura. However, the latter is observed in only about 5% of the population; it is this observation which led to testing the involvement of the CADASIL gene in the mechanisms of this condition. The involvement of this gene in a form of migraine with or without aura was of considerable diagnostic and therapeutic interest because of the frequency of migraine with aura and of migraine without aura in the general population.

Other Vascular (Cerebral Infarct) and/or Dementia Pathologies of Unknown Etiology This group corresponds to a very large number of patients in neurology, psychiatric and internal medicine departments and it is everything to do reasonable to think that Notch3 or a partner in this signaling pathway may be involved in these conditions for the reasons stated above.

Familial Paroxytic Ataxia

The situation is the same as for FHM. A gene responsible for this condition has been located in the same region of chromosome 19 and Notch3 could be implicated in this condition.

Moreover, the mutations of this gene are responsible for developmental abnormalities which are well known in other species as well as for neoplastic-type pathologies. Malformative and/or neoplastic syndromes in which there may be demonstrated, a rearrangement of the region which contains this gene might be major candidates for the search for an involvement of this gene in their physiopathology.

These disorders may be grouped under the name of "disorders linked to the Notch3 receptor".

In some cases, this may involve disorders having a multigenic origin but in which the modifications of Notch3 might contribute to the onset of the pathology or to its worsening.

The present invention relates, first of all, to an isolated nucleotide sequence, characterized in that it is chosen from:
a) the sequences encoding the human Notch3 protein and its allelic variants,
b) the sequences encoding a fragment of these proteins and having at least 10 bases,
c) the human Notch3 genomic sequences and its alleles,
d) the sequences exhibiting at least 80%, and preferably at least 90%, homology with the sequences (a) and (c),
e) the fragments of the sequences (c) or (d) having at least 10 bases,
f) the sequences which hybridize with a sequence of (a) to (e).

It should be understood that the present invention does not relate to the genomic nucleotide sequences in their natural chromosomal environment, that is to say in the natural state; they are sequences which have been isolated, that is to say that they were collected directly or indirectly, for example by copying (cDNA), their environment having been at least partially modified.

Thus, this may also involve both cDNA and genomic DNA which is partially modified or carried by sequences which are at least partially different from the sequences carrying them naturally.

These sequences may also be described as being "non-natural".

"Nucleic sequence" is understood to mean a natural isolated, or synthetic, fragment of DNA and/or RNA designating a precise linkage of nucleotides, modified or otherwise, making it possible to define a fragment, a segment or a region of a nucleic acid.

"Allelic variant" of the protein is understood to mean all the mutated proteins and the polymorphisms which may exist in a human being, which are obtained in particular by truncation, substitution, deletion or addition of amino, acid residues, as well as the artificial variants.

According to the invention, the nucleic sequence fragments may in particular encode domains of the protein or may be used as probe or as primer in methods of detection, identification or amplification. These fragments have a minimum size of 10 bases and fragments of 20 bases, preferably 30 bases, will be preferred.

According to the invention, the homology is solely of the statistical type; it means that the sequences exhibit at least 80%, and preferably 90%, of nucleotides in common.

The hybridization conditions should make it possible, according to the invention, to ensure at least 95% homology.

More particularly, the present invention relates to a nucleotide sequence chosen from:
a) the sequences encoding a polypeptide comprising the amino acids according to the sequence in FIG. 1,
b) the nucleic sequences corresponding to FIG. 1,
c) a fragment of a sequence according to (a) or (b) containing at least 10 bases, and
d) a sequence which contains, relative to the sequences (a), (b) or (c), at most 20 partial mutations.

FIG. 1. represents the sequences of Notch3 as were sequenced on a normal genome.

The sequences are identified by references which make it possible to position them relative to each other using FIG. 3.

As regards the special remarks on (a), (b), (c) and (d), the previous remarks apply.

The invention also relates to the fragments of these sequences, in particular sequences encoding polypeptides which have retained all, or part of the activity of the Notch3 protein.

Among the particularly advantageous sequences, there may be mentioned those encoding domains or combinations of domains of the Notch3 protein, that is to say the sequences:

"EGF" repeats
"Notch/lin12" repeats
"cdc10/SW16" repeats or the transmembrane sequence.

Among the advantageous sequences are in particular the sequence encoded by the second transcript which will be described in the text which follows, the said transcript having an estimated size of between 1.3 and 2.4 kb.

These sequences may be identified with reference in particular to FIG. 2 which schematically represents the organization of Notch3.

These partial sequences can be used for numerous applications, as described below, especially for preparing Notch-type or different types of protein constructs but also for preparing, for example, truncated Notch-like proteins which will serve as lure for the Notch3 ligand or as agonist for the protein.

It is also possible to envisage using these protein sequences for their intrinsic effects; thus, the EGF domains are present in other proteins, especially other receptors; reference may be made for example to Iain D. Campbell,. Current Biology, 3: 385–392 (1993) for other applications of the EGF sequences in question.

While the sequences described are in general normal sequences, the invention also relates to the mutated sequences insofar as they contain at least one point mutation and preferably less than 20 mutations in total.

Preferably, the present invention relates to the nucleotide sequences in which the point mutations are not silent, that is to say that they lead to a modification of the amino acid encoded relative to the normal sequence. Still more preferably, these mutations affect amino acids which structure the Notch3 protein or the corresponding fragments thereof, that is to say in particular the mutations which suppress the cysteines or, on the contrary, which make them appear, but also the mutations which change the character of the protein, either from the charge point, of view, or from the hydrophobicity point of view.

The present invention also relates to the mutations which may occur in the promoter and/or regulatory sequences of the human Notch3 gene, which may have effects on the expression of the protein.

Examples of such mutations will be described in the text which follows.

In general, the present invention relates to both the normal Notch3 protein and the mutated Notch3 proteins, as well as to their fragments and to the corresponding DNA and RNA sequences, that is to say the alleles.

It should be noted that the Northern blot study of the expression of this gene in human tissues reveals two transcripts. One having a size estimated at 7.5–9.5 kb is present in all the tissues tested; the other, whose size is between 1.3 and 2.4 kb, is detected only in some parts of the central nervous system. The present invention relates to these two transcripts.

Among the nucleotide fragments, there may be mentioned the intron genomic sequences of the Notch3 gene and more particularly the joining sequences between the introns and the exons, especially as are represented in Table A; and finally, the present invention relates to all the primers which may be deduced from the preceding nucleotide sequences and which may make it possible to detect them using an amplification method such as the PCR method, especially those presented in Table B.

The present invention also relates to the nucleotide sequences which may contain nonnatural nucleotides, especially sulfur-containing nucleotides for example or having an α or β structure.

Finally, the present invention of course relates to both the DNA and RNA sequences, as well as the corresponding double-stranded DNAs.

As will be described below for some applications, it may be necessary to provide for mixed constructs, protein/DNA/ chemical compound, especially the use of intercalating agents for example; it should be understood that such compounds are covered by the patent as containing a sequence according to the invention.

The present invention also relates to the polypeptide or peptide proteins corresponding to the abovementioned sequences, in a nonnatural form, that is to say that they are not taken in their natural environment but obtained by purification from natural sources or obtained by genetic recombination, as will be described below.

The invention also relates to the same polypeptides or proteins obtained by chemical synthesis and capable of containing nonnatural amino acids.

The present invention relates to the recombinant proteins thus obtained both in a glycosylated and nonglycosylated form and capable of having or otherwise the natural tertiary structure.

In particular, the present invention relates to the Notch3 fragments which exhibit an activity similar to the total receptor, especially the soluble part(s) of said receptor corresponding in particular to their extracellular domain. These may be used especially as a lure in a therapy, as will be described below.

The present invention also relates to the cloning and expression vectors containing a nucleotide sequence as described above.

These cloning and expression vectors may contain elements ensuring the expression of the sequence in a host cell, especially promoter sequences and regulatory sequences which are efficient in said cell (see reference below).

The vector in question may be autonomously replicating or intended to ensure the integration of the sequence into the chromosomes of the host cell.

In the case of autonomously replicating systems, depending on the prokaryotic or eukaryotic host cell, plasmid-type systems or viral systems will preferably be used, it being possible for the viral vectors to be especially adenoviruses, poxviruses or herpesviruses. Persons skilled in the art know the technologies which can be used for each of these viruses (see reference below).

When the integration of the sequence into the chromosomes of the host cell is desired, it will be necessary to provide for, on either side of the nucleotide sequence to be integrated, one or more sequences obtained from the host cell in order to bring about the recombination. These are also methods which are widely described in the prior art. It will be possible, for example, to use plasmid or viral type systems; such viruses will be, for example, retroviruses or AAVs (Adeno-Associated Viruses).

The invention also relates to the prokaryotic or eukaryotic cells transformed by a vector as described above, and this being in order to bring about the expression of a natural or mutated Notch3 protein or, for example, of one of its subunits.

As indicated above, the present invention also relates to the proteins, peptides or polypeptides obtained by culturing the cells thus transformed and recovering the protein expressed, it being possible for said recovery to be carried out intracellularly or extracellularly from the culture medium when the vector: has been designed to bring about the excretion of the protein via for example a "leader" sequence, the protein being in a pre-protein or prepro-protein form. The constructs allowing the secretion of the proteins are known both for prokaryotic systems and eukaryotic systems.

Among the cells which can be used for the production of these proteins, there may of course be mentioned bacterial cells, but also yeast cells, as well as animal cells, in particular mammalian cell cultures, but also insect cells in which methods using baculoviruses for example may be used (see reference below).

The cells thus obtained can make it possible to prepare natural or mutated Notch3 proteins, but also fragments of these proteins, especially polypeptides which may correspond to the different domains in question.

However, the cells transformed as described above may also be used as a model to study the interactions between the Notch gene and its various ligands as well as its influence on the products downstream of the receptor, but in particular they may be used in an application for the selection of products interacting with the natural or mutated Notch3 receptor, as an agonist or an antagonist of this receptor.

This type of cellular model may be produced using genetic engineering techniques. It involves, depending on the type of cells which it is desired to use, cloning the gene in question in its normal form or in its mutated form into an expression vector, whether it is an autonomously replicating vector or an integration vector, said vector containing all the elements allowing the expression of the gene in the cell in question, or the latter having all the elements allowing the expression of the sequence in question.

There are thus obtained eukaryotic or prokaryotic cells expressing the Notch3 protein(s) which, given its characteristics, will be situated like a transmembrane protein whose fine structure will be described in the text which follows, it being possible for said cells to then constitute models which make it possible to test at the same time the interactions Of various ligands with the product of the Notch3 protein or to test synthetic chemical products capable of interacting with the product of the Notch3 gene, and this by adding them to the culture medium for said cells.

It should in particular be noted, that the products in question may also be products with either antagonist or agonist activity.

The use of cellular models to test pharmaceutical products is well known; here again, there is no need to present this type of model in detail.

Another potential application of the characterization of this gene is the possibility of identifying potential ligands for this protein, either because they have a conserved sequence with human Notch3, or because they interact with Notch3 (affinity methods) or partners for this signaling pathway.

These models may be of the in vitro type, for example cultures of human cells, either in a normal culture, or possibly in the form of an isolated organ, such as for example certain types of vessels which may be transformed in order to cause them to express the desired phenotypes.

The present invention also relates to the organisms, such as animals, in particular mice, expressing the phenotype corresponding to the normal or mutated Notch3 of human origin. Here again, these animals may be used as model animals to test the efficacy of certain pharmaceutical products.

The present invention also relates to the products obtained using the preceding cellular models.

There will thus be obtained, depending on the type of interaction determined, therapeutic compositions characterized in that they contain, as active ingredient, a compound with a pro-Notch3 activity; this may be in particular all or part of a polypeptide as were described above or a vector expressing these same polypeptides, or else chemical or biological compounds having a pro-Notch3 activity, a Notch3-like activity or inducing the production of natural Notch3.

It will also be possible to demonstrate therapeutic compositions in which the active ingredient will have an anti-Notch3 action.

This may involve, here again, modified proteins described above which may play the role of a lure, or anti-Notch3 antibodies, in particular when these antibodies recognize the mutated receptors and will, under these conditions, be able to block the activity of the normal receptor.

This may also involve chemical products having an anti-Notch3 activity, or Notch3 antagonists.

In some cases, the use of some of the Notch3 domains may allow a therapeutic approach blocking the activity of the Notch3 receptor when the latter is mutated using soluble receptors which will serve as lure to the natural ligands; in other cases, it will be possible, by expressing the entire receptor, to provide a replacement therapy using either directly the proteins or fragments thereof, or directly expressing the protein, especially via gene therapy and using the vectors which were described above.

In the context of gene therapy, it is also possible to provide for the use of the sequences of the genes or cDNAs described above as "naked"; this technique was in particular developed by the company Vical; it has shown that it was possible, under these conditions, to express the protein in certain tissues without requiring the use of the support for a viral vector in particular.

Still in the context of gene therapy, it is also possible to provide for the use of cells transformed ex vivo, which cells may then be reimplanted either as such or in systems of the organoid type, as is also known in the state of the art. It is also possible to envisage the use of an agent facilitating targeting of the determined cell type, penetration into the cells or transport to the nucleus.

Among the numerous pharmaceutical compounds which can be used, there should be mentioned more particularly, in addition to the ligands for the Notch3 product, the sense or anti-sense sequences interacting with the normal or mutated Notch3 gene, or interacting on the regulation or expression of these genes, it being also possible for said products to interact downstream of the expression products induced by the Notch3 receptors. The soluble sequences corresponding to Notch3 should furthermore be cited.

There should also be mentioned the monoclonal antibodies blocking the Notch3 receptors, in particular the mutated Notch3 receptors, and/or blocking the corresponding ligands and/or the products induced by said receptors which may therefore have pro or anti activities.

It should be recalled that the monoclonal antibodies directed against the Notch3 receptor may, depending on the epitope recognized, have a pro or anti-Notch3 activity which makes them useable in therapeutic compositions.

Finally, the present invention relates, as was said above, more particularly to the methods of diagnosing a predisposition to neurological conditions, especially of the CADASIL type, or of diseases linked to the Notch3 receptor in a patient, characterized in that the presence of a mutation in Notch3 is determined using a biological sample from said patient by analysis of all or part of a nucleic sequence corresponding to said gene, the presence of at least one such mutation being indicative of a predisposition of said patient to neurological conditions or diseases linked to the. Notch3 receptor.

Other diagnostic methods can make it possible to characterize, by means of antibodies, the deposit expected in the basal membrane of the vascular smooth muscle cells, a deposit which might consist of the Notch3 protein itself or one of its cleavage products.

Among the desired mutations, there may be mentioned more particularly the mutations referenced in Table C and FIG. 3.

The nucleic acid sequences may be either genomic DNA, a cDNA or an mRNA.

As was said above, among the neurological disorders which may be demonstrated, there is understood more particularly disorders of the cerebrovascular type and especially CADASIL, but the list of certain disorders which might be linked to an abnormality in the Notch3 receptor has been previously given; among these conditions, there may be mentioned most particularly the potential involvement of Notch3 in migraines with or without aura and dementias of currently unknown etiology.

The diagnostic tools based on the present invention may allow a positive and differential diagnosis in a patient taken in isolation or alternatively a presymptomatic diagnosis in an at-risk subject (family history for example), it is also possible to envisage an antenatal diagnosis.

In addition, the detection of a specific mutation may allow an evolutive diagnosis.

The methods which make it possible to demonstrate the mutation in a gene relative to the natural gene are of course very numerous; they may be carried out by studying the genomic DNA, the cDNA and/or the protein. They can be essentially divided into two large categories, the first type of method is that in which the presence of a mutation is detected by comparing the mutated sequence with the corresponding nonmutated natural sequence, and the second type in which the presence of the mutation is detected indirectly, for example, by detecting the mismatches due to the presence of the mutation.

In both cases, the methods in which all or part of the sequence corresponding to Notch3 is amplified prior to the detection of the mutation will be preferred in general; these amplification methods may be carried out by the so-called PCR (see reference below) or PCR-like methods. PCR-like will. be understood to designate all the methods using direct or indirect reproductions of the nucleic acid sequences, or in which the labeling systems have been amplified; these techniques are well known, in general they relate to the amplification of DNA by polymerase; when the original samples is an RNA, it is advisable to carry out a reverse transcription beforehand; a great number of methods allowing this amplification currently exists, for example the so-called nucleic acid sequence-based amplification (NASBA) and transcription mediated amplification (TMA) methods which are well known to persons skilled in the art.

Table B gives the sequences of the PCR primers which make it possible to amplify the exons as well as the temperatures for the PCR reactions.

A general methodology for amplification of the sequences will be described in the examples.

Test for Point Mutations

In addition to the direct sequencing of the mutation, various methods may be used. The techniques will be briefly cited:
1) test for "Single Strand Conformation Polymorphisms" (SSCP) (see reference below) or denaturing gradient gel electrophoresis (DGGE).
2) the methods based on a cleavage of the mismatched regions (enzymatic cleavage by S1 nuclease, chemical cleavage by various compounds such as piperidine or osmium tetroxide, and the like.
3) heteroduplex detection by electrophoresis,
4) methods based on the use in hybrication of allele-specific oligonucleotide (ASO) probes.

Other well known methods based on hybrication techniques can be used.

Test for Deletion, Inversion or Duplication Type Rearrangements

Other well known methods based on the techniques of hybridization with the aid of genomic probes, of cDNA probes, of oligonucleotide probes, of riboprobes, of so-called capture probes or of so-called detection probes, may be used for the test for this type of rearrangement.

Another diagnostic approach which can be used when DNA from several subjects of the same family is available is based on the method of linkage analysis which makes it possible to calculate the risk which a subject belonging to a linked family has of being a carrier or otherwise of the diseased gene. This analysis may be carried out with poly- morphic markers situated in the immediate vicinity of the gene, or intragenic polymorphic markers.

It is important to recall that in the CADASIL families, the existence of mutations in the Notch3 gene corresponds to mutations which change amino acids which are essential for the function of the protein for which it encodes.

Moreover, in the examples, the situations of the mutations currently detected are indicated, but it is possible that other mutations exist in the Notch3 gene which have not yet been detected but which should lead to the same types of risks from the pathological point of view.

In any case, the mutated Notch3 proteins may exhibit an antigenicity which is different from that of the natural protein.

It is therefore possible to carry out a diagnosis or a prognosis of a susceptibility to neurological, in particular cerebrovascular, disorders of the CADASIL type and disorders linked to the Notch3 receptor, by detecting the product of the mutated gene for Notch3; this type of detection can be carried out, for example, with the aid of monoclonal or polyclonal antibodies. Under these conditions, it is possible to detect and assay the abnormal product of the Notch3 gene by well known methods, RIA or ELISA for example; these technologies being known, they will not be further developed beforehand in the text which follows. Antibodies directed against the normal protein could also be used if the deposit present in the arteries of the skin corresponded to the Notch3 protein or to one of its cleavage products.

The present invention also relates to the labeled monoclonal or polyclonal antibodies corresponding to all or part of the mutated proteins so as to serve as imaging agent in vivo or ex vivo on biological samples.

Thus, it appears that the granular masses present in the basals of the vascular smooth muscle cells are due to an accumulation of the abnormal protein and the test for this protein with the aid of antibodies, either in biopsies or in vivo, is of a diagnostic interest.

Methods Based on the Detection of the Product of the Gene

The mutations of the Notch3 gene may be responsible for various modifications of the product of this gene, modifications which can be used for a diagnostic approach. Briefly, the protein may be truncated, reduced in size or absent; its properties, in particular its antigenicity, may be modified. All these modifications may be used in a diagnostic approach using several well known methods based on the use of mono- or polyclonal antibodies which recognize the normal protein or mutated variants, and this using the study of protein extracts or of tissue sections (for example skin biopsies), or studies carried out in vivo (imaging with the aid of antibodies coupled to a molecule which is detectable in PET-scan type imaging, and the like).

The polyclonal or monoclonal antibodies may be obtained by immunological reaction of a human or animal organism with an immunogenic agent consisting of a protein or a polypeptide capable of being obtained from prokaryotic or eukaryotic cells transformed by a vector as described above. Preferably, the immunogenic agent consists of a specific polypeptide of the mutated form of the Notch protein whose sequence is chosen from the polypeptide sequences comprising at least one mutation chosen from the mutations corresponding to FIG. 3 or to Table C.

The present invention finally relates to therapeutic compositions containing, as active ingredient, a compound with a pro-Notch3 activity, especially as described above, as well as therapeutic compositions containing, as active ingredient, a compound with an anti-Notch3 activity.

Figure 4:
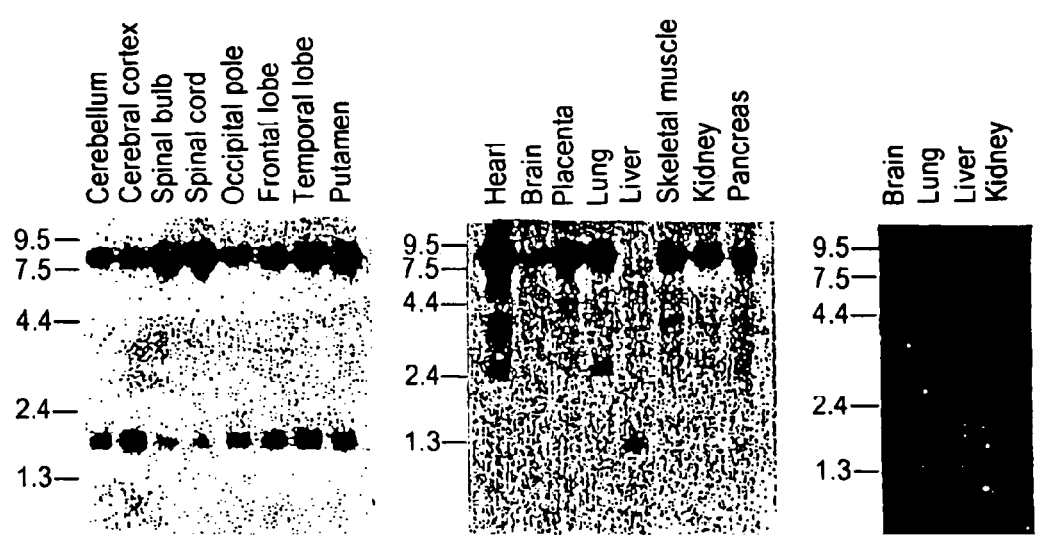

Other characteristics and advantages of the present invention will appear on reading the examples below, with reference to the accompanying drawings in which:

FIG. 1 reproduces the cDNA sequence (SEQ ID NO:1) of human Notch3 as well as the corresponding protein sequence (SEQ ID NO:2). Panels 1A–1H present the sequences in consecutive order, with the seciuences on each panel following directly from the preceding panel;

FIG. 2 represents the general structure of the product of the Notch3 gene as well as the mutations which were detected by aligning the human cDNA clones with mouse Notch3, A—mouse Notch3 gene with its 34 EGF domains, 3 Notch/Lin12 repeats and 6 cdc10 repeats, as well as the transmembrane domain, B—at the bottom, 8 of the human cDNAs with the identifications corresponding to FIG. 1, at the top, the alignment of some genomic sequences with the cDNA of at least 29 exons, the origins of the various fragments appear at the bottom of FIG. 4;

the various clones are available commercially or through libraries;

the clones 261623; 153875; 149693 are available from the IMAGE consortium;

the clone C-32b03 is available from GENEXPRESS (Généthon, Evry, France);

the clones p28–20; CNA-20 are available from CLONTECH;

FIG. 3 schematically represents the situation and the nature of the mutations involved in CADASIL;

FIG. 4 represents a "Northern blot" analysis, the Northern blots containing 2 μg per line of human poly (A$^+$) DNA, from left to right:

of various brain tissues, of various adult organs, of various fetal organs;

they are hybridized with p28–20, a Notch3 human 1.45 kb cDNA probe; a 7.5 to 9.5 kb transcript is detected in all the tissues, both adult and fetal, with the exception of the liver, the transcript is weakly expressed in the brain tissue in the middle and on the right;

on the contrary, on the left, not only are transcripts of all the tissues observed, but also the presence of a transcript of between 2.4 and 1.3 kb whose presence has never been mentioned and which may be of a very high importance is observed.

EXAMPLE 1

Scheme for the Isolation and Analysis of the Notch3 Gene

Following the remarks and the analysis which were summarized at the beginning of the description as regards the location of the gene, murine cDNA probes were used to isolate the cDNA for the human Notch3 gene, and then genomic clones whose sequences could be aligned with it and with the murine cDNA sequences.

Additional information on the sequences were obtained from a cDNA fragment (884Na4) obtained by cDNA selection on YAC (884g1) and from two genomic fragments (J431NH and J432NH) which were obtained by subcloning of BAC 13J4 NotI-HindIII fragments.

In the screening of the (dbest) data bank with all the sequences, it has been possible to identify additional clones (IMAGE clones, Genexpress).

The coding sequence of the human Notch3 gene, which is highly homologous to the corresponding murine gene, is represented in FIG. 1.

Table A schematically represents the structure of the gene, specifying the sequence and the position of the exon-intron junctions.

In this table, the first exon corresponds to a sequence whose 5' end was not completely cloned, likewise for exon 33.

It should be noted that alternative cDNAs may exist which correspond to the known phenomenon of alternative splicing.

This sequence contains 34 EGF domains, 3 Notch/lin12 repeats, as well as 3 cdc10 ankyrin-like repeats. The human and murine proteins exhibit 90.5% identity on the sequence currently available. A 1.45 kb partial human cDNA probe containing the EGF-like domains reveals a ubiquitous transcript in the fetal tissues, as well as in the human adult tissues whose size of between 7.5 and 9.5 kb is similar to the murine transcript (FIG. 4).

This probe reveals another transcript in certain subregions of the brain whose size is estimated at between 1.3 and 2.4 kb (FIG. 4).

EXAMPLE 2

Study of the Mutations

In order to study the extent of the mutations in the Notch3 gene on CADASIL, the possible presence of a substantial genomic DNA rearrangement was first studied using various combinations of enzymes and of Notch3 probes.

No drastic rearrangement could be detected in the CADASIL patients, that is why point mutations were then tested for.

Thus, the mutations of the total coding sequence of the Notch3 gene in the genomic DNA were studied using a combination of SSCP method and heteroduplex analysis in 51 CADASIL patients with no family relationship. 28 of them belong to families for which the evidence for a relationship with chromosome 19 has been demonstrated and 33 exhibit ultrastructural lesions of the wall of the arterioles of the skin (presence of osmiophilic granular deposits in the basal membrane of the vascular smooth muscle cells).

All the splicing junctions, except 3, were analyzed. In addition, direct sequencing of the PCR products of exon 4 and its splicing sites was carried out on all the patients.

Impairments which were compatible with corresponding mutations were found in 42 patients (82%), said mutations not being observed in any of the 200 control chromosomes. For 26 patients, it was possible to analyze one or more which were related, affected or otherwise, and in each case it was established that the mutation segregated with the CADASIL phenotype. There are 29 different mutations, of which 20 are described for the first time. They include 24 missense mutations which appear in 40 patients, which mutations should replace (16) one amino acid with an additional or mutated cysteine (8) one of the 6 cysteine residues, which are the key elements of the EGF domains.

Two of the mutations at the 5' splicing site in the latter two patients should normally affect the splicing of exon 4. The last three mutations are missense mutations which appear in 3 patients simultaneously with the mutations described above.

Patient 21 carries 2 distinct mutations which change an arginine to cysteine at codon 141 in EGF 3 and which changes a conserved glycine to alanine at codon 288 in EGF 7. This patient's pedigree was not available; it was not therefore possible to study the cosegregation of these two mutations.

Patient 29 carries a first mutation in EGF 4 which changes an arginine 182 to cysteine and a second which changes a highly conserved alanine 1852 to threonine in the cdc10 domain. These two mutations segregated with the disease.

The last patient 55 is a carrier of two distinct mutations in the EGF domains, which change a cysteine (224) to a tryptophan and a nonconserved leucine (497) to a serine residue.

Although the latter three missense mutations are not detected in the 200 control chromosomes, they may involve rare polymorphisms given the presence also of missense mutations which mutate or create cysteine residues.

It should be noted that most of these 26 mutations having a pathogenic effect lie exclusively in the EGF parts. 41% of these mutations (11 out of 26) appearing in 25 patients are situated in exon 4 and 65% (17 out of 26) lie in the first 6 EGF domains (see in particular FIG. 3.

FIG. 3 allows the detection to characterize the main mutations detected, the nomenclature chosen indicates the position of the mutation as well as the corresponding modifications of the protein.

As was indicated above, the fact that a Notch gene is involved in neurological disorders in adults appears completely surprising since Notch is mainly known to be involved during development in drosophila. None of the CADASIL families studied up until now exhibits developmental abnormalities.

EXAMPLE 3

Detection of the Mutations in Patients by the SSCP Method

The oligonucleotides used as primers were synthesized from intron-exon joining sequences (Table B) so as to amplify genomic fragments of about 200 bp. The sequences of the PCR primers are given below (Table A).

The analyses can be carried out using DNA extracted from blood samples or any other tissue.

The amplification reactions are carried out in a final volume of 25 µl containing 100 ng of genomic DNA, 0.5 µm of each primer, 150 µg of a mixture of 4dNTPs, Taq polymerase 1XPCR from Cetus, 1 U Taq polymerase (BRL), 1.5 µCi αdCTP labeled with P33 according to a protocol comprising 30 identical cycles (94° C., 15 s; 65° C., 15 s; 72° C., 15 s).

For some of the primers, an "annealing" temperature of 70° C. should be used, as indicated in Table A.

The PCR products are denatured in 50% formamide and separated by electrophoresis in a 6% nondenaturing polyarylamide gel.

After autoradiography, the SSCP bands obtained in the patients are compared with those of healthy controls in search of abnormal variants. Their analysis can be used as a diagnostic approach. These variants can then be sequenced if necessary.

TABLE A

Exon-intron structure of the Notch3 gene
(sequences and positions of the exon-intron junctions)

| Splice Acceptor Site Intron/Exon | Exon (size) | Position | Splice Donor Site Exon/Intron | |
|---|---|---|---|---|
| | 1 | 1–196 | CTGCAT/gtgagggc laAlaAl | (SEQ ID NO:3) |
| (SEQ ID NO:4) cccacacag/CCCCCC aProPr | 2 (79) | 197–275 | CTGCCT/gtgagtgcc aCysLe | (SEQ ID NO:5) |
| (SEQ ID NO:6) gcccacag/GTGCCC uCysPr | 3 (143) | 276–418 | TCCGAG/gtgagagg heArgG | (SEQ ID NO:7) |
| (SEQ ID NO:8) ccctccag/GCCCTG lyProA | 4 (339) | 419–757 | TTCCTG/gtgagtga euProG | (SEQ ID NO:9) |
| (SEQ ID NO:10) cttgttag/GGTTTG lyPheG | 5 (123) | 758–880 | GGACAG/gtgggcac rpThrG | (SEQ ID NO:11) |
| (SEQ ID NO:12) tgccacag/GCCAGT lyGlnP | 6 (234) | 881–1114 | AGACTG/gtgagtgg ysThrG | (SEQ ID NO:13) |
| (SEQ ID NO:14) cttcccag/GCCTCC lyLeuL | 7 (156) | 1115–1270 | CTATCG/gtgagggg erIleG | (SEQ ID NO:15) |
| (SEQ ID NO:16) tccggcag/GCGCCA lyAlaA | 8 (187) | 1271–1456 | TGGCAG/gtgggtgg etAlaG | (SEQ ID NO:17) |
| (SEQ ID NO:18) tgcccag/GCTTCA lyPheT | 9 (114) | 1457–1570 | CCTCGG/gtgaggac roSerG | (SEQ ID NO:19) |
| (SEQ ID NO:20) caccccag/GCTTCA lyPheS | 10 (114) | 1571–1684 | CCGAGG/gtgaggcg laGluG | (SEQ ID NO:21) |
| (SEQ ID NO:22) ccccacag/GCTTTG lyPheG | 11 (234) | 1685–1918 | CCACAG/gtgggacc hrThrG | (SEQ ID NO:23) |

TABLE A-continued

Exon-intron structure of the Notch3 gene
(sequences and positions of the exon-intron junctions)

| Splice Acceptor Site<br>Intron/Exon | Exon<br>(size) | Position | Splice Donor Site<br>Exon/Intron | |
|---|---|---|---|---|
| (SEQ ID NO:24) gcccctag/GTGTGA<br>lyValA | 12 (111) | 1919–2029 | TCACAG/gtgggcaa<br>heThrG | (SEQ ID NO:25) |
| (SEQ ID NO:26) ctccccag/GGCCCC<br>lyProL | 13 (193) | 2030–2222 | TGGCGG/gtgagggc<br>oGlyGl | (SEQ ID NO:27) |
| (SEQ ID NO:28) cctgccag/GTTCCG<br>yPheAr | 14 (152) | 2223–2374 | TCCAGG/gtgtgtac<br>alGlnG | (SEQ ID NO:29) |
| (SEQ ID NO:30) cccaacag/GACGTC<br>lyArgG | 15 (114) | 2375–2488 | GGCAAG/gtatgccac<br>rpGlnG | (SEQ ID NO:31) |
| (SEQ ID NO:32) taccccag/GCCCAC<br>lyProA | 16 (156) | 2489–2644 | ACCCCA/gtgagtgca<br>spProA | (SEQ ID NO:33) |
| (SEQ ID NO:34) gtccgcag/ACCCAT<br>snProC | 17 (226) | 2645–2870 | CCCCAG/gtgggcgg<br>rProSe | (SEQ ID NO:35) |
| (SEQ ID NO:36) cgctccag/CTCCTG<br>rSerCy | 18 (202) | 2871–3072 | TGCCAG/gtgggtgg<br>CysGln | (SEQ ID NO:37) |
| (SEQ ID NO:38) ccctccag/ACGCTG<br>ThrLeu | 19 (148) | 3073–3220 | AGATCG/gtgagtgg<br>InIleG | (SEQ ID NO:39) |
| (SEQ ID NO:40) ctttgcag/GGGTGC<br>lyValA | 20 (185) | 3221–3405 | TGTGAG/gtaaggggg<br>CysGlu | (SEQ ID NO:41) |
| (SEQ ID NO:42) cactgaag/TGTCTT<br>CysLeu | 21 (133) | 3406–3538 | CGCTGG/gtatgcca<br>hrLeuG | (SEQ ID NO:43) |
| (SEQ ID NO:44) tcccccag/GGGTGC<br>lyValL | 22 (258) | 3539–3796 | TCTCAG/gttaacct<br>heSerG | (SEQ ID NO:45) |
| (SEQ ID NO:46) tcgctcag/GTCCTC<br>lyProA | 23 (119) | 3797–3915 | GCCCAG/gtaggtgtg<br>AlaGln | (SEQ ID NO:47) |
| (SEQ ID NO:48) gaccccag/CCGTTC<br>ProPhe | 24 (556) | 3916–4481 | TTGCAA/gtgagccc<br>rCysAs | (SEQ ID NO:49) |
| (SEQ ID NO:50) cccaccag/CCCGGT<br>nProVa | 25 (333) | 4482–4814 | GATCGG/gtgagtgac<br>lIleG | (SEQ ID NO:51) |
| (SEQ ID NO:52) tccctgcag/CTCGGT<br>ySerVal | 26 (155) | 4815–4969 | TGCGGG/gtgcggcc<br>alArgG | (SEQ ID NO:53) |
| (SEQ ID NO:54) tgctcttag/GGGAGC<br>lyGluP | 27 (223) | 4970–5192 | CATGAA/gtgagaac<br>yMetLy | (SEQ ID NO:55) |
| (SEQ ID NO:56) tccgccag/GAACAT<br>sAsnMe | 28 (85) | 5193–5277 | CTAAG/gtactgcc<br>LeuLys | (SEQ ID NO:57) |
| (SEQ ID NO:58) cccctccag/GTAGAG<br>ValGLu | 29 (162) | 5278–5440 | GCCCAG/gtcagtgac<br>lyProA | (SEQ ID NO:59) |
| (SEQ ID NO:60) ccctgcag/ATGGCT<br>spGlyP | 30 (305) | 5441–5745 | TTCCAG/gtgagata<br>PheGln | (SEQ ID NO:61) |
| (SEQ ID NO:62) tgtcctag/ATTCTC<br>IleLeu | 31 (148) | 5746–5893 | AGCTTG/gtaggttg<br>luLeuG | (SEQ ID NO:63) |
| (SEQ ID NO:64) ccctccag/GGAAAT<br>lyLysS | 32 (99) | 5894–5992 | AGCAAG/gtgagccc<br>SerLys | (SEQ ID NO:65) |
| (SEQ ID NO:66) cccccag/GAGGAG<br>GluGlu | 33 | 5993– | | |

TABLE B

Sequences of the primers used for the screening of the mutations of the Notch3 gene

| Exon | Size | Domain | | Primers | | PCR product size |
|---|---|---|---|---|---|---|
| 1 | | Signal peptide | EOF | AAGGAGGGAGGAGGGGAG | (SEQ ID NO:66) | 125 |
| | | | EOR | TGGGGGTTCTTGCACTCC* | (SEQ ID NO:67) | |
| | | | EOF | AAGGAGGGAGGAGGGGAG | (SEQ ID NO:68) | 163 |
| | | | EORBIS | GGTTCCTGCCTCCCATGA* | (SEQ ID NO:69) | |
| 2 | 79 | EGF1 | EIF | TCCTCCACCTTCCTTCAC* | (SEQ ID NO:70) | 148 |
| | | | EIR | ACACACAGGGCCCACTGGT* | (SEQ ID NO:71) | |
| 3 | 143 | EGR 1–2 | N1F | TGTGCTGCCCAACCAAGCCA* | (SEQ ID NO:72) | 224 |
| | | | N1R | ACTGACCACACCCCCGACTA* | (SEQ ID NO:73) | |
| 4 | 339 | EGF 2–5 | N2A F | TAGTCGGGGGTGTGGTCAGT* | (SEQ ID NO:74) | 192 |
| | | | N2A R | TCATCCACGTCGCTTCGGCA | (SEQ ID NO:75) | |
| | | | CNA F | ATGGACGCTTCCTCTGCTC | (SEQ ID NO:76) | 167 |
| | | | CNA R | ACATAGTGGCCCTGTGTAGC | (SEQ ID NO:77) | |
| | | | CNA F | ATGGACGCTTCCTCTGCTCC | (SEQ ID NO:78) | 295 |
| | | | N3AR | CCTCTGACTCTCCTGAGTAG* | (SEQ ID NO:79) | |
| 5 | 123 | EGF 5–6 | N23Fbis | TGACCATCCTTGCCCCCTT* | (SEQ ID NO:80) | 241 |
| | | | N23 R | CTGGCCTGTGGCACACAGAT* | (SEQ ID NO:81) | |
| 6 | 234 | EGF 6–8 | N13A F | TGGACTGCTGCATCTGTGTG* | (SEQ ID NO:82) | 191 |
| | | | N13A R | ACACGCCTGTGGCACAGTCA | (SEQ ID NO:83) | |
| | | | N13B F | GAGCTGCAGTCAGAATATCG | (SEQ ID NO:84) | 145 |
| | | | N13B R | ATCCATGGCTCCCTGCAGAG* | (SEQ ID NO:85) | |
| 7 | 156 | EGF 8–10 | N24 F | CAGAGCAGGAAGATCTGCCT* | (SEQ ID NO:86) | 229 |
| | | | N24 R | CATTCACAGACGACGGAGcT* | (SEQ ID NO:87) | |
| 8 | 187 | EGF10–11 | N3 F | ATCGCACTCCATCCGGCA* | (SEQ ID NO:88) | 212 |
| | | | N3 R | ACCCACCTGCCATACAGA* | (SEQ ID NO:89) | |
| 9 | 114 | EGF11–12 | N25AF | CGTTCACACCATAGGGTAGC* | (SEQ ID NO:90) | 215 |
| | | | N25AR | CCCCTTCCCAGACATGTCTT | (SEQ ID NO:91) | |
| 10 | 114 | EGF12–13 | N25BF | CTTGTCGGACTGTCATTGG | (SEQ ID NO:92) | 195 |
| | | | N25BR | GTGTACTGCTCTCACCCTT* | (SEQ ID NO:93) | |
| 11 | 234 | EGF13–15 | N4AF | ATTGGTCCGAGGCCTCACTT* | (SEQ ID NO:94) | 213 |
| | | | N4AR | ACCTGGCTCTCGCAGCGTGT | (SEQ IS NO:95) | |
| | | | N4B R | CCATTCCCAACCCCTCTGTG | (SEQ ID NO:96) | 199 |
| | | | N4B F | TGCCTGTGCTCCTGGCTACA* | (SEQ ID NO:97) | |
| 12 | 111 | EGF15–16 | N5 F | TGGCCACTCCATGCCATGTT* | (SEQ ID NO:98) | 166 |
| | | | N5 R | TCTCATGGCAGCCACTTGCC* | (SEQ ID NO:99) | |
| 13 | 193 | EGF16–18 | N14 F | ATGAGTGTGCTTCCAGCCCA* | (SEQ ID NO:100) | 258 |
| | | | N14 R | GCAGTGTCTGAGGCTGAGAA* | (SEQ ID NO:101) | |
| 14 | 152 | EGF18–19 | N6 F | TCCCTGGCCTGACTACCTTC* | (SEQ ID NO:102) | 207 |
| | | | N6 R | CTGCAGAGGAAGGTGAGGT* | (SEQ ID NO:103) | |
| 15 | 114 | EGF 19–20 | N26BF | AAGGCTATCCTGCTTCC* | (SEQ ID NO:104) | 183 |
| | | | N26BR | GAGGAGGAGGGAAGAGAA* | (SEQ ID NO:105) | |
| 16 | 156 | EGF20–22 | S13FB1S | AGGATGTGGACGAGTGTGCT | (SEQ ID NO:106) | 195 |
| | | | N26CR | GCTTAATGACTGTGTTC* | (SEQ ID NO:107) | |
| 17 | 226 | EGF22024 | N15A F | TCAGACTGGGCTAATGGGGG* | (SEQ ID NO:108) | 257 |
| | | | N15A R | TCGCAGTGGAAGCCTCCGTA | (SEQ ID NO:109) | |
| | | | N15BF | GATGTGGATGAGTGCCTGAG | (SEQ ID NO:110) | 166 |
| | | | N15BR | GTCCTGCTCTTCAAGCAGA* | (SEQ ID NO:111) | |
| 18 | 202 | EGF24–25 | N27F | GATCCTCCCTCCCACTCCTT* | (SEQ ID NO:112) | 256 |
| | | | N27R | AGGTCCCCAGTAACTCCA* | (SEQ ID NO:113) | |

TABLE B-continued

Sequences of the primers used for the screening
of the mutations of the Notch3 gene

| Exon | Size | Domain | Primers | | | PCR product size |
|---|---|---|---|---|---|---|
| 19 | 148 | EGF25–27 | N22 F | ACTGACTCTAAGTGCTTCCC* | (SEQ ID NO:114) | 240 |
| | | | N22 R | AGCAGGAGGTACGTGCATGA* | (SEQ ID NO:115) | |
| 20 | 185 | EGF27–28 | N7 F | TGTTCCTGTGCCACTCTCCT* | (SEQ ID NO:116) | 249 |
| | | | N7 R | ACCTCCTCTTCCCTCTCCT* | (SEQ ID NO:117) | |
| 21 | 133 | EGF28–29 | N8 F | TCTGTGTCCCACTAAGCTGA* | (SEQ ID NO:118) | 237 |
| | | | N8 R | CAAGAGGAAATGAAGACAGC* | (SEQ ID NO:119) | |
| 22 | 258 | EGF29–31 | N9A F | TTCCTCTTGACCACCCCTCG* | (SEQ ID NO:120) | 217 |
| | | | N9A R | TGGCAGGCACCTGAGCGACA | (SEQ ID NO:121) | |
| | | | N9B F | CAGGATACACTGGTTTGCGC | (SEQ ID NO:122) | 209 |
| | | | N9B R | TGCCACGTTATGGATCAGCC* | (SEQ ID NO:123) | |
| 23 | 119 | EGF31–32 | N10 F | GATCTACATGCTCCCGCTCG* | (SEQ ID NO:124) | 178 |
| | | | N10 R | TACTCCTCCTCCATAGGCCG* | (SEQ ID NO:125) | |
| 24 | 566 | EGF32–34 Lin12 N1–3 | N16AFTR | CGTTCTGGGGTCCGCGTT | (SEQ ID NO:126) | 249 |
| | | | N16DR | AAGCGCAGCGGAAGAAGGGC | (SEQ ID NO:127) | |
| | | | N16FF | GCCCTTCTTCCGCTGCGCTT | (SEQ ID NO:128) | 230 |
| | | | N16FR | ACTGCAGCGCCTCGCATTGC | (SEQ ID NO:129) | |
| | | | N16GF | CTGCGACCGCGAGTGCAACA | (SEQ ID NO:130) | 239 |
| | | | N16HR | ATAGACAGACGGATCGAT* | (SEQ ID NO:131) | |
| 25 | 331 | Lin12 N3 | N21CF | CTCTCTGCCTCACCCTT* | (SEQ ID NO:132) | 207 |
| | | | N21CR | GCTGGAACGCAGTAGCT | (SEQ ID NO:133) | |
| | | | N21DF | TGCTCACAGTGCTGCTG | (SEQ ID NO:134) | 223 |
| | | | N21DR | CACGGCTTTTCCAGGTG* | (SEQ ID NO:135) | |
| 26 | 155 | | N34F | TTTGAGCCCTCTGGTCC* | (SEQ ID NO:136) | 306 |
| | | | N34R | AAGAGCAGGAAGCAGAG* | (SEQ ID NO:137) | |
| 27 | 222 | TM | N28Fbis | TCCCTCTGCTTCCTGCTCTT* | (SEQ ID NO:138) | 291 |
| | | | N23r | TCACAAGGTCCCCGTAGTCA* | (SEQ ID NO:139) | |
| 28 | 85 | | J5N3F | CTCACATCCCTCTTCCCAT* | (SEQ ID NO:140) | 203 |
| | | | J5N3R | ATCACGCCCATCATCCACTG* | (SEQ ID NO:141) | |
| 29 | 163 | Cdc10N1 | L24bisF | CAGCACCAAAGGGTG* | (SEQ ID NO:142) | 241 |
| | | | L24bisR | CATCCCTTTGGGAGG* | (SEQ ID NO:143) | |
| 30 | 305 | Cdc10N1–3 | N17AF | ATGGCTTCACCCCGCTAATG | (SEQ ID NO:144) | 176 |
| | | | N17AR | AGCCAGGTGCAAAGCAGTCT | (SEQ ID NO:145) | |
| | | | N17BF | TCAGCTTGGGGCACGGACTG | (SEQ ID NO:146) | 239 |
| | | | N17BR | GCATCGGCTGTGACAGCTGT | (SEQ ID NO:147) | |
| 31 | 148 | Cdc10N4–5 | N26FBIS | TGTTCCTGCCATGACCCCT* | (SEQ ID NO:148) | 239 |
| | | | N26RBIS | CAGGTGACACTAACCCAGTC* | (SEQ ID NO:149) | |
| 32 | 98 | Cdc10n5–6 | N31F | TCCTGACCTCTCTCCCCTTC* | (SEQ ID NO:150) | 178 |
| | | | N31R | AATGGCGCTGTGCCACTGcT* | (SEQ ID NO:151) | |
| 33 | | Cdc10N6 NLS PEST | N32AF | GCTACTGTTAGCTGGGGTTT* | (SEQ ID NO:152) | 214 |
| | | | N32AR | TGATCCAGCAAGCGCACGAT | (SEQ ID NO:153) | |
| | | | N32EFTER | TCACCGACCACCTGGACA | (SEQ ID NO:154) | 425 |
| | | | N32DR | ACCAAGCTGTGCCAGAGA | (SEQ ID NO:155) | |
| | | | N32DF | TCCAAGAAGAGCAGGAGG | (SEQ ID NO:156) | 246 |
| | | | N32DR | ACCAAGCTGTGCCAGAGA | (SEQ ID NO:157) | |

TABLE B-continued

Sequences of the primers used for the screening of the mutations of the Notch3 gene

| Exon | Size | Domain | Primers | | | PCR product size |
|---|---|---|---|---|---|---|
| | | | N32BF | CAGTGTCTCTGGCACAGCT | (SEQ ID NO:158) | 248 |
| | | | N32BR | TCCTGGGACTGCCAGGTAA | (SEQ ID NO:159) | |
| | | | N32CF | AGCTGCTCAACCCAGGGA | (SEQ ID NO:160) | 229 |
| | | | N32CR | GTGGATTCGGACCAGTCT | (SEQ ID NO:161) | |
| | | | N32GF | GAATCCCCTGAGCACT | (SEQ ID NO:162) | 235 |
| | | | N32GR | CTAAGAACTGACGAGC | (SEQ ID NO:163) | |

*intronic primers

TABLE C

Notch3 mutations in CADASIL patients

| Patient | Evidence of linkage | SMC lesions | Notch3 nt[a] | NotcH mutation | Effect | Exon | Domain | Segregation |
|---|---|---|---|---|---|---|---|---|
| 52* | nd | nd | 224 | TGT-->TAT | $C_{49}$-->Y* | N2 | EGF1 | nd |
| 56 | nd | + | 291 | TGG-->TGT | $W_{71}$-->C | N3 | EGFI | nd |
| 11 | + | nd | 406 | CGT-->TGT | $R_{110}$-->C | N3 | EGF2 | + |
| 3 | + | + | 419(−2) | AG-->GG | abnormal splicing of exon 4 ? | N4 | | + |
| 39 | nd | + | 419(−2) | AG-->CG | abnormal splicing of exon 4 ? | N4 | | nd |
| 10 | + | + | 475 | CGC-->TGC | $R_{133}$-->C | N4 | EGF3 | + |
| 20 | nd | + | 475 | CGC-->TGC | $R_{133}$-->C | N4 | EGF3 | nd |
| 46 | + | nd | 475 | CGC-->TGC | $R_{133}$-->C | N4 | EGF3 | + |
| 6 | + | nd | 499 | CGC-->TGC | $R_{141}$-->C | N4 | EGF3 | + |
| 12 | + | + | 499 | CGC-->TGC | $R_{141}$-->C | N4 | EGF3 | + |
| 19 | + | nd | 499 | CGC-->TGC | $R_{141}$-->C | N4 | EGF3 | + |
| 21* | nd | + | 499 | CGC-->TGC | $R_{141}$-->C | N4 | EGF3 | nd |
| | | | 941 | GGC-->GCG | $G_{288}$-->A* | NS | EGF7 | nd |
| 38 | + | nd | 499 | CGC-->TGC | $R_{141}$-->C | N4 | EGF3 | + |
| 49 | + | + | 499 | CGC-->TGC | $R_{141}$-->C | N4 | EGF3 | + |
| 26 | + | + | 514 | TGC-->CGC | $C_{146}$-->R | N4 | EGF3 | + |
| 4 | + | + | 535 | CGC-->TGC | $R_{153}$-->C | N4 | EGF3 | + |
| 50 | nd | + | 535 | CGC-->TGC | $R_{153}$-->C | N4 | EGF3 | + |
| 9* | + | + | 583 | CGC-->TGC | $R_{169}$-->C* | N4 | EGF4 | + |
| 15* | + | nd | 583 | CGC-->TGC | $R_{169}$-->C* | N4 | EGF4 | + |
| 24 | + | nd | 583 | CGC-->TGC | $R_{169}$-->C | N4 | EGF4 | + |
| 36* | nd | + | 583 | CGC-->TGC | $R_{169}$-->C* | N4 | EGF4 | nd |
| 48 | nd | + | 583 | CGC-->TGC | $R_{169}$-->C | N4 | EGF4 | nd |
| 1 | + | nd | 589 | GGT-->TGT | $G_{171}$-->C | N4 | EGF4 | + |
| 45* | + | + | 622 | CGC-->TGC | $R_{182}$-->C* | N4 | EGF4 | + |
| 47* | nd | + | 622 | CGC-->TGC | $R_{182}$-->C* | N4 | EGF4 | nd |
| 29* | + | + | 622 | CGC-->TGC | $R_{182}$-->C | N4 | EGF4 | + |
| | | | 5632 | GCT-->ACT | $A1852 >T*$ | N30 | cdc10 | + |
| 41 | nd | + | 631 | TGT-->CGT | $C_{185}$-->R | N4 | EGF4 | nd |
| 57 | nd | + | 712 | TGC-->AGC | $C_{212}$-->S | N4 | EGF5 | nd |
| 8 | + | nd | 742 | TGT-->GGT | $C_{222}$-->G | N4 | EGF5 | + |
| 55 | nd | nd | 749 | TGT-->TAT | $C_{224}$-->Y | N4 | EGF5 | + |
| | | | 1568 | TCG-->TTG | $S_{497}$-->L | N9 | EGF12 | − |
| 14 | + | + | 851 | TAT-->TGT | $Y_{258}$-->C | N5 | EGF6 | + |
| 54* | nd | + | 1703 | TGT-->TAT | $C_{542}$-->Y* | N11 | EGF13 | nd |
| 17* | + | + | 1750 | CGC-->TGC | $R_{558}$-->C* | N11 | EGF14 | + |
| 18* | + | + | 1750 | CGC-->TGC | $R_{558}$-->C* | N11 | EGF14 | + |
| 31* | nd | + | 1810 | CGC-->TGC | $R_{578}$-->C* | N11 | EGF14 | + |
| 43 | nd | nd | 2260 | CGC-->TGC | $R_{728}$-->C | N14 | EGF18 | nd |
| 25 | + | + | 3031 | CGC-->TGC | $R_{985}$-->C | N18 | EGF25 | + |
| 42 | nd | + | 3031 | CGC-->TGC | $R_{985}$-->C | N18 | EGF25 | nd |
| 7 | + | nd | 3094 | CGC-->TGC | $R_{1006}$-->C | N19 | EGF26 | + |
| 35 | nd | nd | 3169 | CGC-->TGC | $R_{1031}$-->C | N19 | EGF26 | + |
| 33 | nd | nd | 3769 | CGC-->TGT | $R_{1231}$-->C | N22 | EGF31 | nd |
| 58* | nd | + | 3859 | TGC-->CGC | $C_{1261}$-->R* | N23 | EGF32 | nd |

*patient and mutation previously reported[7]
SMC: smooth muscle cell

REFERENCES FOR THE VARIOUS METHODS CITED ABOVE

Polymerase Chain Reaction (PCR)
Saiki et al., Science 239, p. 487, 1988+reference manual.
SSCP
Orita et al., Proc. Natl. Acad. Sci. USA, 86, p. 2766–2770, 1989.

Techniques for Detection of Mutations Based on the Demonstration of Mismatches
chemical cleavage
enzymatic cleavage (S1 nuclease)
heteroduplex
Allele Specific Oligonucleotide probes (ASO)

References:
Cotton et al., Proc. Natl. Acad. Sci. USA, 85, 4397, 1988
Sherk et al., Proc. Natl. Acad. Sci. USA, 72, 989, 1975
Cariello, Hum. Genet., 42, 726, 1988

Cloning Vectors and Basic Molecular Biology Techniques
Current protocols in molecular biology, Eds F. M. Ausubel, R. Brent, R. E. Kingston, D. D. Moore, S. G. Seldman, J. A. Smith and K. Struhl, Published by Green Publishing Associates and Wiley Interscience, 1st edition 1987, John Wiley and sons
Molecular cloning. A laboratory manual, J. Sambrook, E F Fritsch and T. Mariatis, 2nd edition, 1989, Cold Spring Harbor Laboratory Press

---

The invention claimed is:

1. A method of diagnosing the presence of Cerebral Autosomal Dominant Arteriopathy with Subcortical Infarcts and Leukoencephalopathy (CADASIL) or a predisposition to CADASIL in a patient, said method comprising
   providing a biological sample from said patient; and
   analyzing all or part of a nucleic acid sequence corresponding to a Notch3 gene in the biological sample to determine whether at least one mutation in the Notch3 gene is present,
   wherein the presence of at least one mutation is indicative of an increased risk of the presence of CADASIL.

2. The method according to claim 1, wherein said at least one mutation is selected from the group of mutations described in Table C.

3. The method according to claim 1, in which the nucleic acid sequence analyzed is a genomic DNA, a cDNA, or an mRNA.

4. The method according to claim 1, wherein said analysis comprises hybridization using at least one oligonucleotide probe specific for the mutated sequence.

5. The method according to claim 1, wherein the presence of a mutation is detected by comparison with the corresponding nonmutated natural sequence.

6. The method according to claim 1, wherein said analysis is carried out by sequencing.

7. The method according to claim 1, wherein said analysis is carried out by electrophoretic migration.

8. The method according to claim 7, wherein said electrophoretic migration is Single Strand Conformation Polymorphisms (SSCP) or Denaturing Gradient Gel Electrophoresis (DGGE).

9. The method according to claim 1, wherein said analysis is carried out by a methodology intended to detect a truncation of the protein.

10. The method according to claim 1, wherein all or part of the nucleic acid sequence of the Notch3 gene is amplified prior to detection of said at least one mutation.

11. The method according to claim 10, wherein the amplification is carried out by PCR or PCR-like amplification.

12. A method of diagnosing the presence of CADASIL or a predisposition to CADASIL in a patient, said method comprising
provoking a biological sample from said patient; and
analyzing all or part of a nucleic acid sequence corresponding to a Notch3 gene in the biological sample to determine whether at least one mutation in the Notch3 gene is present,
wherein said analyzing comprises amplifying all or part of the nucleic acid sequence of the Notch3 gene prior to detection of said at least one mutation, said amplifying being performed with at least one primer consisting of the sequence of any one of SEQ ID NO:66–163, and
wherein the presence of at least one mutation is indicative of an increased risk of the presence of CADASIL.

13. The method according to claim 12, wherein the presence of a mutation is detected by comparison with the corresponding nonmutated natural sequence.

14. The method according to claim 12, wherein said analysis is carried out by electrophoretic migration.

15. The method according to claim 14, wherein said electrophoretic migration is Single Strand Conformation Polymorphisms (SSCP) or Denaturing Gradient Gel Electrophoresis (DGGE).

16. A method of detecting the presence or absence of a mutation in a nucleic acid in a biological sample, comprising:
a) analyzing all or part of a nucleic acid corresponding to a Notch3 gene in the biological sample and a control sample to determine whether at least one mutation is present in the biological sample nucleic acid
wherein the control sample comprises a Notch3 gene comprising SEQ ID NO: 1; and
b) determining the presence or absence of one or more mutations in the biological sample nucleic acid compared to the control sample nucleic acid.

17. The method of claim 16, wherein the presence of a mutation in the Notch3 gene is indicative of the neurological condition is CADASIL.

18. The method of claim 16, wherein the mutation in the Notch3 gene is selected from the group consisting of the mutations listed in Table C.

19. The method of claim 16, wherein the mutation in the nucleic acid results in a polypeptide comprising an amino acid sequence that differs from SEQ ID NO: 2 by one or more mutations selected from the group consisting of:
R133C, R141C, C146R, R153C, R169C, R182C, Y258C, R558C, and R985C.

20. A method of detecting the presence or absence of CADASIL in a subject, comprising detecting the presence or absence of a mutation in a Notch3 gene in a biological test sample obtained from the subject, comprising:
a) analyzing all or a part of a nucleic acid corresponding to a Notch3 gene in the biological sample and a control sample to determine whether at least one mutation is present in the biological sample nucleic acid
wherein the control sample comprises a Notch3 gene comprising SEQ ID NO: 1; and
b) determining the presence or absence of one or more mutations in the Notch3 gene in the biological sample compared to the Notch3 gene in the control sample nucleic acids.

21. The method of claim 20, wherein the mutation in the gene is selected from the group consisting of the mutations listed in Table C.

22. The method of claim 20, wherein the mutation in the nucleic acid results in a polypeptide comprising an amino acid sequence that differs from SEQ ID NO: 2 by one or more mutations selected from the group consisting of:
R133C, R141C, C146R, R153C, R169C, R182C, Y258C, R558C, and R985C.

* * * * *

UNITED STATES PATENT AND TRADEMARK OFFICE
CERTIFICATE OF CORRECTION

PATENT NO.        : 7,138,234 B2
APPLICATION NO. : 10/356625
DATED             : November 21, 2006
INVENTOR(S)       : Elisabeth Tournier-Lasserve et al.

It is certified that error appears in the above-identified patent and that said Letters Patent is hereby corrected as shown below:

Claim 20, col. 102, line 26, "acids" should read --acid--.

Signed and Sealed this

Twenty-third Day of January, 2007

JON W. DUDAS
*Director of the United States Patent and Trademark Office*